(12) United States Patent
Remmers et al.

(10) Patent No.: US 11,129,745 B2
(45) Date of Patent: Sep. 28, 2021

(54) ORAL APPLIANCES AND METHODS OF USE

(71) Applicant: ZST Holdings, Inc., Calgary (CA)

(72) Inventors: John Remmers, Sedona, AZ (US); Shouresh Charkhandeh, Edmonton (CA); Peter Santosham, Calgary (CA); Terry Macartney, Calgary (CA); Sabina Bruehlmann, Calgary (CA)

(73) Assignee: ZST Holdings, Inc., Calgary (CA)

( * ) Notice: Subject to any disclaimer, the term of this patent is extended or adjusted under 35 U.S.C. 154(b) by 725 days.

(21) Appl. No.: 15/648,711

(22) Filed: Jul. 13, 2017

(65) Prior Publication Data

US 2018/0000629 A1   Jan. 4, 2018

Related U.S. Application Data

(62) Division of application No. 14/369,352, filed as application No. PCT/US2012/072093 on Dec. 28, 2012, now abandoned.

(Continued)

(51) Int. Cl.
  *A61F 5/56*   (2006.01)
  *A61C 19/06*   (2006.01)
  *A61B 5/00*   (2006.01)

(52) U.S. Cl.
  CPC ............ *A61F 5/566* (2013.01); *A61B 5/4818* (2013.01); *A61C 19/06* (2013.01); *Y10T 29/49* (2015.01)

(58) Field of Classification Search
  CPC . A61F 5/56; A61F 5/566; A61C 19/06; A61C 7/002; A61B 5/4818

(Continued)

(56) References Cited

U.S. PATENT DOCUMENTS 2,171,695 A   9/1939   Harper
4,376,628 A   3/1983   Aardse (Continued)

FOREIGN PATENT DOCUMENTS

CN   1602970   4/2005
CN   101143115   3/2008

(Continued)

OTHER PUBLICATIONS

Almeida, F.R., et al., "Effect of a Titration Polysomnogram on Treatment Success with a Mandibular Repositioning Appliance," Journal of Clinical Sleep Medicine, vol. 5, No. 3, 2009, pp. 198-204.

(Continued)

*Primary Examiner* — Keri J Nelson
(74) *Attorney, Agent, or Firm* — Meunier Carlin & Curfman LLC

(57) ABSTRACT

Oral appliances, and systems and methods, which include oral appliances are described herein. An example oral appliance device for treatment of a sleep disorder or condition in a subject can include an upper portion configured to receive at least one maxillary tooth of the subject, and a lower portion configured to receive at least one mandibular tooth of the subject. The upper and lower portions are engageable such that the portions maintain a restricted orientation relative to each other when engaged, and the engaged restricted orientation is configured to maintain the mandible of the subject in a predetermined clinically beneficial orientation relative to the maxilla.

20 Claims, 9 Drawing Sheets

Related U.S. Application Data

(60) Provisional application No. 61/582,046, filed on Dec. 30, 2011.

(58) Field of Classification Search
USPC .......................................................... 128/848
See application file for complete search history.

(56) References Cited

U.S. PATENT DOCUMENTS

| | | |
|---|---|---|
| 4,602,905 A | 7/1986 | O'Keefe |
| 4,901,737 A | 2/1990 | Toone |
| 5,030,098 A | 7/1991 | Branford |
| 5,154,609 A | 10/1992 | George |
| 5,313,960 A | 5/1994 | Tomasi |
| 5,365,945 A | 11/1994 | Halstrom |
| 5,409,017 A | 4/1995 | Lowe |
| 5,427,117 A | 6/1995 | Thornton |
| 5,513,986 A | 5/1996 | Feltham et al. |
| 5,537,994 A | 7/1996 | Thornton |
| 5,566,683 A | 10/1996 | Thornton |
| 5,570,704 A | 11/1996 | Buzzard et al. |
| 5,611,355 A | 3/1997 | Nilsen |
| 5,642,737 A | 7/1997 | Parks |
| 5,666,960 A | 9/1997 | Fredberg et al. |
| 5,671,733 A | 9/1997 | Raviv et al. |
| 5,678,567 A | 10/1997 | Thornton et al. |
| 5,755,219 A | 5/1998 | Thornton |
| 5,782,240 A | 7/1998 | Raviv et al. |
| 5,794,627 A | 8/1998 | Frantz et al. |
| 5,816,799 A | 10/1998 | Parker |
| 5,823,193 A | 10/1998 | Singer et al. |
| 5,826,579 A | 10/1998 | Remmers et al. |
| 5,829,441 A | 11/1998 | Kidd |
| 5,846,212 A | 12/1998 | Beeuwkes et al. |
| 5,868,138 A | 2/1999 | Halstrom |
| 5,884,628 A | 3/1999 | Nilsen |
| 5,921,942 A | 7/1999 | Remmers et al. |
| 5,941,247 A | 8/1999 | Keane |
| 5,953,713 A | 9/1999 | Behbehani |
| 5,954,048 A | 9/1999 | Thornton |
| 5,961,447 A | 10/1999 | Raviv et al. |
| 5,983,892 A | 11/1999 | Thornton |
| 6,012,920 A | 1/2000 | Woo |
| 6,041,784 A | 3/2000 | Halstrom |
| 6,055,986 A | 5/2000 | Meade |
| 6,109,265 A | 8/2000 | Frantz et al. |
| 6,155,262 A | 12/2000 | Thornton et al. |
| 6,161,542 A | 12/2000 | Halstrom |
| 6,273,859 B1 | 8/2001 | Remmers et al. |
| 6,290,654 B1 | 9/2001 | Karakasoglu |
| 6,305,376 B1 | 10/2001 | Thornton |
| 6,325,064 B1 | 12/2001 | Thornton |
| 6,374,824 B1 | 4/2002 | Thornton |
| 6,450,167 B1 | 9/2002 | David et al. |
| 6,516,805 B1 | 2/2003 | Thornton |
| 6,634,353 B1 | 10/2003 | Knebelman et al. |
| 6,729,335 B1 | 5/2004 | Halstrom |
| 6,769,910 B1 | 8/2004 | Pantino |
| 6,877,513 B2 | 4/2005 | Scarberry et al. |
| 7,146,982 B2 | 12/2006 | Mousselon et al. |
| 7,174,895 B2 | 2/2007 | Thornton et al. |
| 7,282,027 B2 | 10/2007 | Sotos et al. |
| 7,328,698 B2 | 2/2008 | Scarberry et al. |
| 7,328,705 B2 | 2/2008 | Abramson |
| 7,331,349 B2 | 2/2008 | Brady et al. |
| 7,357,635 B2 | 4/2008 | Belfor et al. |
| 7,396,333 B2 | 7/2008 | Stahmann et al. |
| 7,637,262 B2 | 12/2009 | Bailey |
| 7,712,468 B2 | 5/2010 | Hargadon |
| 7,832,403 B2 | 11/2010 | Halstrom et al. |
| 7,841,987 B2 | 11/2010 | Sotos et al. |
| 8,001,973 B2 | 8/2011 | Sotos et al. |
| 8,025,063 B2 | 9/2011 | Sotos et al. |
| 8,037,886 B2 | 10/2011 | Sotos et al. |
| 8,226,407 B2 | 7/2012 | Hanewinkel et al. |
| 8,550,816 B2 | 10/2013 | Hanewinkel et al. |
| 8,646,447 B2 | 2/2014 | Martin et al. |
| 8,666,467 B2 | 3/2014 | Lynn et al. |
| 9,468,378 B2 | 10/2016 | Lynn et al. |
| 10,265,013 B2 | 4/2019 | Lim |
| 10,265,014 B2 | 4/2019 | Lim |
| 10,537,463 B2 | 1/2020 | Kopelman |
| 2002/0165462 A1 | 11/2002 | Westbrook et al. |
| 2003/0224313 A1 | 12/2003 | Bergersen |
| 2004/0030224 A1 | 2/2004 | Sotos et al. |
| 2004/0162704 A1 | 8/2004 | Siegel et al. |
| 2005/0028827 A1 | 2/2005 | Halstrom |
| 2005/0081859 A1 | 4/2005 | Scarberry et al. |
| 2005/0175709 A1 | 8/2005 | Baty et al. |
| 2005/0175954 A1 | 8/2005 | Zacher |
| 2005/0241646 A1 | 11/2005 | Sotos et al. |
| 2006/0003292 A1 | 1/2006 | Lauren et al. |
| 2006/0020178 A1 | 1/2006 | Sotos et al. |
| 2006/0063981 A1 | 3/2006 | Sotos et al. |
| 2006/0155205 A1 | 7/2006 | Sotos et al. |
| 2006/0266356 A1 | 11/2006 | Sotos et al. |
| 2007/0068534 A1 | 3/2007 | Bailey et al. |
| 2007/0179395 A1 | 8/2007 | Sotos et al. |
| 2007/0183572 A1 | 8/2007 | Drummond et al. |
| 2007/0239056 A1 | 10/2007 | Moore |
| 2007/0283967 A1 | 12/2007 | Bailey |
| 2007/0283973 A1 | 12/2007 | Longley |
| 2008/0053461 A1 | 3/2008 | Hirotsuka et al. |
| 2008/0064008 A1 | 3/2008 | Schmitt |
| 2008/0076094 A1 | 3/2008 | Hindin |
| 2008/0236597 A1 | 10/2008 | Bergersen |
| 2008/0269832 A1 | 10/2008 | Wong et al. |
| 2009/0078257 A1 | 3/2009 | Bhat et al. |
| 2009/0078274 A1 | 3/2009 | Bhat et al. |
| 2009/0123886 A1 | 5/2009 | Vaska |
| 2009/0241969 A1 | 10/2009 | Walker |
| 2010/0018538 A1 | 1/2010 | Sotos et al. |
| 2010/0101583 A1 | 4/2010 | Chen et al. |
| 2010/0154802 A1 | 6/2010 | Fuselier |
| 2010/0163043 A1 | 7/2010 | Hart et al. |
| 2010/0204614 A1 | 8/2010 | Lindquist et al. |
| 2010/0217426 A1 | 8/2010 | Sotos et al. |
| 2010/0240982 A1 | 9/2010 | Westbrook et al. |
| 2010/0300457 A1 | 12/2010 | Horchover |
| 2010/0316973 A1 | 12/2010 | Remmers et al. |
| 2011/0005526 A1 | 1/2011 | Garabadian et al. |
| 2011/0168186 A1 | 7/2011 | Halstrom |
| 2011/0217674 A1 | 9/2011 | Hanewinkel et al. |
| 2011/0232652 A1 | 9/2011 | Levendowski et al. |
| 2011/0295083 A1 | 12/2011 | Doelling et al. |
| 2013/0023797 A1 | 1/2013 | Hanewinkel et al. |
| 2014/0114146 A1 | 4/2014 | Hanewinkel et al. |
| 2014/0180036 A1 | 6/2014 | Bukkapatnam et al. |
| 2015/0039045 A1 | 2/2015 | Ni et al. |
| 2015/0068536 A1 | 3/2015 | Remmers et al. |
| 2015/0164682 A1 | 6/2015 | Remmers et al. |
| 2016/0022205 A1 | 1/2016 | Remmers et al. |
| 2018/0078403 A1 | 3/2018 | Remmers et al. |
| 2019/0167467 A1 | 6/2019 | Remmers et al. |
| 2019/0246975 A1 | 8/2019 | Remmers et al. |

FOREIGN PATENT DOCUMENTS

| | | |
|---|---|---|
| CN | 100486545 | 5/2009 |
| CN | 101917924 | 12/2010 |
| CN | 102481181 | 5/2012 |
| CN | 103841888 | 6/2014 |
| CN | 104066400 | 9/2014 |
| EP | 1832306 | 9/2007 |
| JP | 2001-524852 | 12/2001 |
| JP | 2007-275349 A | 10/2007 |
| WO | 97/16151 | 5/1997 |
| WO | 1998/046177 | 10/1998 |
| WO | 2005025417 | 3/2005 |
| WO | 2005/107590 | 11/2005 |
| WO | 2005/115266 | 12/2005 |
| WO | 2008/030965 | 3/2008 |
| WO | 2008/151374 | 12/2008 |
| WO | 2010/072387 | 7/2010 |

(56) References Cited

FOREIGN PATENT DOCUMENTS

| WO | 2010/087824 | 8/2010 |
|---|---|---|
| WO | 2010/141868 | 12/2010 |
| WO | 2010/141957 | 12/2010 |
| WO | 2011/005299 | 1/2011 |
| WO | 2011/082346 | 7/2011 |
| WO | 2011/147985 | 12/2011 |
| WO | 2013/188660 | 12/2013 |
| WO | 2014/159236 | 10/2014 |
| WO | 2014/170855 | 10/2014 |

OTHER PUBLICATIONS

Cartwright, R.D., "Predicting Response to the Tongue Retaining Device for Sleep Apnea Syndrome," Arch. Otolaryngol., vol. 111, 1985, pp. 385-388.

Chan, A.S.L., et al., "Nasopharyngoscopic evaluation of oral appliance therapy for obstructive sleep apnoea," European Respiratory Journal, vol. 35, No. 4, 2010, pp. 836-842.

Clark, S.A., et al., "Assessment of Inspiratory Flow Limitation Invasively and Noninvasively during Sleep," American Journal of Respiratory and Critical Care Medicine, vol. 158, 1998, pp. 713-722.

De Backer, et al., "Functional imaging using computational fluid dynamics to predict treatment success of mandibular advancement devices in sleep-disordered breathing", Journal of Biomechanics, 2007, vol. 40, pp. 3708-3714.

Dort, L.C., et al., "Mandibular advancement and obstructive sleep apnoea: a method for determining effective mandibular protrusion," European Respiratory Journal, vol. 27, No. 5, 2006, pp. 1003-1009.

Friedman, M., et al., "Compliance and Efficacy of Titratable Thermoplastic versus Custom Mandibular Advancement Devices," Otolaryngology—Head and Neck Surgery, vol. 147, No. 2, 2012, pp. 379-386.

Kim, Y.-K., et al., "The influence of the amount of mandibular advancement in the application of mandibular advancement device for obstructive sleep apnea patients," Sleep Medicine and Psychophysiology, vol. 18, No. 6, 2011, pp. 29-34. (English Abstract).

Kuna et al., "Evaluation of an oral mandibular advancement titration appliance," Oral Surg Oral Med Oral Pathol Oral Radiol Endod, 2006, vol. 101, No, 5, pp. 593-603.

Levendowski, D.J., et al., "Initial Evaluation of a Titration Appliance for Temporary Treatment of Obstructive Sleep Apnea," J. Sleep Disord. Ther., vol. 1, Issue 1, 2011, 8 pages.

Liu, Y., et al., "Cephalometric and physiologic predictors of the efficacy of an adjustable oral appliance for treating obstructive sleep apnea," American Journal of Orthodontics and Dentofacial Orthopedics, vol. 120, No. 6, 2001, pp. 639-647.

Marklund, M., et al., "Treatment Success With a Mandibular Advancement Device Is Related to Supine-Dependent Sleep Apnea," Chest, vol. 114, No. 6, 1998, pp. 1630-1635.

Morgenstern, C., et al., "Assessment of Changes in Upper Airway Obstruction by Automatic Identification of Inspiratory Flow Limitation During Sleep," IEEE Transactions on Biomedical Engineering, vol. 56, No. 8, 2009, pp. 2006-2015.

Otsuka, R., et al., "A comparison of responders and nonresponders to oral appliance therapy for the treatment of obstructive sleep apnea," American Journal of Orthodontics and Dentofacial Orthopedics, vol. 129, No. 2, 2006, pp. 222-229.

Pételle, B., et al., "One-Night Mandibular Advancement Titration for Obstructive Sleep Apnea Syndrome," American Journal of Respiratory and Critical Care Medicine, vol. 165, 2002, pp. 1150-1153.

Remmers, J., et al., "Remotely Controlled Mandibular Protrusion during Sleep Predicts Therapeutic Success with Oral Appliances in Patients with Obstructive Sleep Apnea," Sleep, vol. 36, No. 10, 2013, pp. 1517-1525A.

Tsai, W.H., et al., "Remotely Controlled Mandibular Positioner Predicts Efficacy of Oral Appliances in Sleep Apnea," American Journal of Respiratory and Critical Care Medicine, vol. 170, No. 4, 2004, pp. 366-370.

Tsuiki, S., et al., "Optimal positive airway pressure predicts oral appliance response to sleep apnoea," European Respiratory Journal, vol. 35, No. 5, 2010, pp. 1098-1105.

Vázquez, J.-C., et al., "Automated analysis of digital oximetry in the diagnosis of obstructive sleep apnoea," Thorax., vol. 55, 2000, pp. 302-307.

Examination Report No. 1, dated Sep. 13, 2016, received in connection with AU Patent Application No. 2012362189.

Examination Report No. 2, dated Aug. 10, 2017, received in connection with AU Patent Application No. 2012362189.

Office Action dated Sep. 17, 2018, received in connection with Canadian Application No. 2,862,641.

Office Action dated Jun. 21, 2019, received in connection with Canadian Application No. 2,862,641.

Communication Pursuant to Rule 164(1) EPC, dated Sep. 4, 2015, received in connection with EP Patent Application No. 12861941.8.

Search Report, dated Feb. 9, 2016, received in connection with EP Patent Application No. 12861941.8.

Communication Pursuant to Rule 94(3) EPC, dated Jun. 29, 2018, received in connection with EP Patent Application No. 12861941.8.

Communication Pursuant to Rule 94(3) EPC, dated Sep. 13, 2019, received in connection with EP Patent Application No. 12861941.8.

International Preliminary Report on Patentability and Written Opinion, dated Jul. 1, 2014, received in connection with related International Application No. PCT/US2012/072093.

International Search Report and Written Opinion, dated May 15, 2013, received in connection with related International Application No. PCT/US2012/072093.

Zaber Actuator Position Characterization, Published Oct. 8, 2009, accessed at [HTTP:https://zaber/com/technical-articles/actuator-precision-characterization] (Year:2009).

Galil Motion Control, Inc., User Manual "DMC-40x0" ManulalRev. 1.0b Published May 2008 (Year 2008).

Communication pursuant to Rule 94(3) EPC, dated Jun. 15, 2021, received in connection with EP Patent Application No. 12861941.8, 4 pages.

ORAL APPLIANCES AND METHODS OF USE

CROSS-REFERENCE TO RELATED APPLICATION

This application is divisional of U.S. application Ser. No. 14/369,352, filed on Jun. 27, 2014, which is a 35 U.S.C. § 371 national phase of International Application No. PCT/US2012/072093, filed on Dec. 28, 2012, which claims the benefit of U.S. Provisional Patent Application No. 61/582,046, filed on Dec. 30, 2011, entitled "Oral Appliances and Methods of Use," the disclosures of which are expressly incorporated herein by reference in their entireties.

TECHNICAL FIELD

This document relates to oral appliances and methods of using and manufacturing oral appliances for treatment of sleep disordered breathing and related sleep conditions.

BACKGROUND

Sleep disordered breathing, including obstructive sleep apnea and central sleep apnea, high upper airway resistance, and snoring are examples of sleep disorders or conditions that often cause significant morbidity and mortality. For example, sleep disordered breathing and related conditions can produce excessive daytime sleepiness, headache, depression, irritability, and cognitive impairments. As well, these disorders have been shown to be risk factors for cardiovascular diseases, including hypertension, atrial fibrillation, stroke and heart failure.

SUMMARY

Provided are oral appliances, and systems and methods, which include oral appliances. The oral appliances can be used to treat sleep conditions and disorders by reducing or eliminating at least one symptom or manifestation or cause of the sleep disorder or condition.

An example oral appliance device for treatment of a sleep disorder or condition in a subject includes an upper portion configured to receive at least one maxillary tooth of the subject and a lower portion configured to receive at least one mandibular tooth of the subject.

The upper and lower portions are engageable such that the portions maintain a restricted orientation relative to each other when engaged. The engaged restricted orientation is configured to maintain the mandible of the subject in a predetermined clinically beneficial orientation relative to the maxilla. The sleep disorder or condition treated by the oral appliance may include sleep apnea, obstructive sleep apnea, central sleep apnea, high upper airway resistance and/or snoring.

Optionally, the upper and lower portions have a fixed predetermined geometry. The fixed predetermined geometry of the upper and lower portions may function to position the mandible of the subject in the predetermined clinically beneficial orientation relative to the maxilla when the upper and lower portions are engaged.

The fixed predetermined geometry of the upper and lower portions are optionally based on a data set obtained from the subject when the mandible of the subject is positioned into the clinically beneficial orientation relative to the maxilla. The data set is optionally obtained while the subject is sleeping. Whether or not the subject is sleeping, the data set may be obtained with the use of a device such as a titration device.

The example oral appliance device may further comprise a connector. The connector is optionally configured to connect the upper and lower portions to position the mandible of the subject in the predetermined clinically beneficial orientation relative to the maxilla when the upper and lower portions are engaged. Optionally, the connector has a fixed predetermined geometry. The fixed predetermined geometry of the connector is optionally based on a data set obtained from the subject when the mandible of the subject is positioned into the clinically beneficial orientation relative to the maxilla. The data set is optionally obtained while the subject is sleeping. Whether or not the subject is sleeping, the data set may be obtained with the use of a device such as a titration device. Optionally, at least a portion of the connector is removably fixed to the upper or lower portions. Optionally, at least a portion of the connector is non-removably fixed to the upper or lower portions.

The restricted orientation optionally maintains a minimal level of repositioning of mandible relative to the maxilla in at least one degree of freedom. In some examples, the restricted orientation maintains a minimal level of repositioning of mandible relative to the maxilla in two, three, four, five or six degrees of freedom.

For example, the engaged restricted orientation may maintain a minimal level of mandibular protrusion in the subject. The minimal level of protrusion is optionally at least 1.0 mm or greater. The minimal level of protrusion may orient the mandible and maxilla of the subject such that at least one symptom or manifestation of the sleep disorder or condition is reduced or eliminated when the device is used in the subject.

In addition, or independent of, maintaining a minimal level of mandibular protrusion, the restricted orientation may optionally maintain a minimal level of bite opening, i.e., rotation of the mandible about the temporomandibular joint. Optionally, the minimal level of bite opening is at least 0.5 degrees or greater. The minimal level of bite opening alone, or in combination with the minimal level of mandibular protrusion, orients the mandible and maxilla of the subject such that at least one symptom or manifestation of the sleep disorder or condition is reduced or eliminated when the device is used in the subject.

In addition, or independent of, maintaining a minimal level of mandibular protrusion and/or a minimal level of bite opening, the restricted orientation may optionally maintain a minimal level of occlusal plane separation in the subject, i.e., separation of the maxillary and mandibular teeth. Optionally, the minimal level of occlusal plane separation is at least 1.0 mm or greater. The minimal level of occlusal plane separation alone, or in combination with either or both the minimal level of mandibular protrusion and bite opening, orients the mandible and maxilla of the subject such that at least one symptom or manifestation of the sleep disorder or condition is reduced or eliminated when the device is used in the subject.

The upper portion of the device optionally comprises an upper tray configured to house one or more of the maxillary teeth of the subject, and the lower portion optionally comprises a lower tray configured to house one or more of the mandibular teeth of the subject. Optionally, the upper tray has a geometry configured to communicate with a plurality of the maxillary teeth of the subject, wherein the geometry is at least partially based on a digital scan of the maxillary teeth. Optionally, the lower tray has a geometry configured to communicate with a plurality of the mandibular teeth of the subject, wherein the geometry is at least partially based on a digital scan of the mandibular teeth.

Thus, the device may optionally comprise an upper portion having a fixed predetermined geometry and an upper tray, wherein the upper tray is configured to house one or more teeth of the subject. The lower portion may also have a fixed predetermined geometry that is configured to house one or more teeth of the subject. The fixed predetermined geometry of the upper and lower portions are optionally based on a data set obtained by positioning the mandible of the subject into the clinically beneficial orientation and on at least one digital scan of one or more maxillary and mandibular teeth of the subject.

Also provided is a device for treatment of sleep disorder or condition in a subject comprising an upper portion configured to receive at least one maxillary tooth of the subject and a lower portion configured to receive at least one mandibular tooth of the subject wherein the upper and lower portions are engageable such that the portions maintain a restricted orientation relative to each other when engaged. The engaged restricted orientation is configured to maintain a minimal level of repositioning of mandible relative to the maxilla in at least one degree of freedom. Optionally, the restricted orientation maintains a minimal level of repositioning of the mandible relative to the maxilla in two, three, four, five or six degrees of freedom.

Further provided is a device for treatment of sleep disorder or condition in a subject. The device comprises an upper portion configured to receive at least one maxillary tooth of the subject and a lower portion configured to receive at least one mandibular tooth of the subject. The upper and lower portions are engageable such that the portions maintain a restricted orientation relative to each other when engaged. The engaged restricted orientation is configured to maintain a minimal level of separation of the mandible relative to the maxilla in the occlusal plane. The subject optionally retains his/her pre-device protrusion of the mandible of the subject relative to the maxilla and the subject optionally retains his/her pre-device bite opening angle. Optionally, the upper and lower portions have geometries configured to communicate with a plurality of the maxillary and mandibular teeth respectfully and the geometries are at least partially determined from a digital scan of the maxillary and mandibular teeth respectfully.

Also provided are kits for treatment of a sleep disorder or condition in a subject. An example kit includes a first oral appliance comprising an upper portion configured to receive at least one maxillary tooth of the subject and a lower portion configured to receive at least one mandibular tooth of the subject. The upper and lower portions are engageable such that the portions maintain a restricted orientation relative to each other when engaged. The engaged restricted orientation is configured to maintain a minimal level of repositioning of mandible relative to the maxilla in at least one degree of freedom.

The kit further comprises a second oral appliance having an upper portion configured to receive at least one maxillary tooth of the subject and a lower portion configured to receive at least one mandibular tooth of the subject. The upper and lower portions are engageable such that the portions maintain a restricted orientation relative to each other when engaged. The engaged restricted orientation is configured to maintain a minimal level of repositioning of mandible relative to the maxilla in at least one degree of freedom. Optionally, the restricted orientation of the first and second oral appliances maintain a minimal level of repositioning of the mandible relative to the maxilla in two, three, four, five or six degrees of freedom.

Optionally, the kit further comprises at least one additional oral appliance. Each additional appliance comprises an upper portion configured to receive at least one maxillary tooth of the subject and a lower portion configured to receive at least one mandibular tooth. The upper and lower portions are engageable such that the portions maintain a restricted orientation relative to each other when engaged. The engaged restricted orientation is configured to maintain a minimal level of repositioning of mandible relative to the maxilla in at least one degree of freedom.

One or more of the oral appliances are optionally configured to position the mandible of the subject relative to the maxilla of the subject in a predetermined clinically beneficial orientation. Each oral appliance of a series is optionally configured to progressively position the mandible of the subject relative to the maxilla of the subject towards a predetermined clinically beneficial orientation. The upper and lower portions have geometries configured to communicate with a plurality of the maxillary and mandibular teeth respectfully. The geometries are optionally at least partially determined from a digital scan of the maxillary and mandibular teeth respectfully.

Also provided is an oral appliance for use in titrating the mandible of a subject into a clinically beneficial orientation relative to the maxilla of the subject. Optionally, the upper and lower portions are not engageable and instead allow the portions to move relative to one another in one, two, three, four, five or six degrees of freedom to determine the clinically beneficial orientation. The appliance comprises an upper tray having a geometry configured to communicate with a plurality of the subject's maxillary teeth. The geometry of the upper tray is optionally at least partially determined from a digital scan of the maxillary teeth. The appliance further comprises a lower tray having a geometry configured to communicate with a plurality of the subject's mandibular teeth. Optionally, the geometry of the lower tray is at least partially determined from a digital scan of the mandibular teeth. Optionally, the device is operatively engageable with titration appliance.

Also provided is a device for treatment of a sleep condition or disorder in a subject comprising an upper tray having a geometry configured to communicate with a plurality of the subject's maxillary teeth. The geometry of the upper tray is at least partially determined from a digital scan of the maxillary teeth. The device further comprises a lower tray having a geometry configured to communicate with a plurality of the subject's mandibular teeth. The geometry of the lower tray is at least partially determined from a digital scan of the mandibular teeth.

Optionally, the upper and lower trays are engageable such that the trays maintain a restricted orientation relative to each other when engaged. The engaged restricted orientation is configured to maintain a minimal level of repositioning of the mandible relative to the maxilla in at least one degree of freedom. Optionally, the restricted orientation maintains a minimal level of repositioning of the mandible relative to the maxilla in two, three, four, five or six degrees of freedom.

Also provided are methods for producing a device for treatment of a sleep disorder or condition. An example method optionally comprises positioning the mandible of the subject in a clinically beneficial orientation relative to the maxilla of the subject. The position of the mandible relative to the maxilla is optionally registered. The registration is completed optionally at the time the clinically beneficial position is established (ie during the titration test) or by recreating the clinically beneficial position by use of a jig. The registered position is then used to manufacture a device that positions the mandible in the clinically beneficial orientation relative to the maxilla.

The position of the mandible relative to the maxilla is optionally determined using a two dimensional coordinate system. The two dimensional coordinate system may be established using anatomical landmarks of the maxilla, mandible and the dentition. For example, the two dimensional coordinate system may comprise an axis residing in the occlusal plane of the maxillary teeth and a second axis perpendicular to the occlusal plane of the maxillary teeth. For example, the two dimensional coordinate system optionally includes a first axis residing in the occlusal plane of the maxillary teeth and extends from the inter-incisal space of the upper incisors and substantially along the midline of the maxillary teeth. In this example, the two dimensional coordinate system may also optionally include a second axis residing perpendicular to the occlusal plane of the maxillary teeth and intersecting the first axis at the inter-incisal space of the upper incisors.

The position of the mandible relative to the maxilla may also be determined using a three dimensional coordinate system. The three dimensional coordinate system may be established using anatomical landmarks of the maxilla/mandible and the dentition. For example, the three dimensional coordinate system optionally includes a first axis residing in the occlusal plane of the maxillary teeth and extends from the inter-incisal space of the upper incisors and substantially along the midline of the maxillary teeth. A second axis optionally resides perpendicular to the occlusal plane of the maxillary teeth and intersects the first axis at the inter-incisal space of the upper incisors. A third axis optionally resides in the occlusal plane of the maxillary teeth, is perpendicular to the second axis and intersects the first and second axes at the inter-incisal space of the upper incisors.

The registered position is optionally used to manufacture at least a second device that positions the mandible in the clinically beneficial orientation or into a second or additional clinically beneficial orientation. For example, the mandible of the subject may be positioned into a second clinically beneficial orientation relative the maxilla of the subject. The second position of the mandible relative to the maxilla can be registered. The registered second position is then used to manufacture a device that positions the mandible in the second clinically beneficial orientation relative to the maxilla. Alternatively, the first registered position may be adjusted to create a second registered position, without registering the second position directly on the patient, to manufacture a device that positions the mandible in the second clinically beneficial orientation relative to the maxilla.

A digital scan of one or more maxillary teeth of the subject is optionally obtained and is optionally used with the registered position to manufacture the device. Moreover, a digital scan of one or more mandibular teeth of the subject is optionally obtained. The digital scan of the one or more mandibular teeth is optionally used with the registered position to manufacture the device.

Also provided are methods for treatment of a sleep disorder or condition in a subject. Example methods include positioning an oral appliance that maintains the mandible of the subject in a predetermined clinically beneficial orientation relative to the maxilla of the subject into the mouth of the subject.

The oral appliance may have an upper portion configured to receive at least one maxillary tooth of the subject and a lower portion configured to receive at least one mandibular tooth of the subject. The upper and lower portions are optionally engageable such that the portions maintain a restricted orientation relative to each other when engaged. The engaged restricted orientation maintains the mandible of the subject in a predetermined clinically beneficial orientation relative to the maxilla of the subject.

The predetermined clinically relevant position is optionally determined by titration of the mandible relative to the maxilla while the subject is asleep. The mandible of the subject may also optionally be maintained in a second clinically beneficial orientation relative to the maxilla of the subject.

Furthermore, the mandible of the subject may optionally be maintained in a series of clinically beneficial orientations relative to the maxilla of the subject. In these examples, the second clinically beneficial orientation is optionally maintained by a second oral appliance. The series of successive clinically relevant beneficial orientations may be maintained by a series of successive oral appliances. The second, or each successive, oral appliance includes an upper portion configured to receive at least one maxillary tooth of the subject and a lower portion configured to receive at least one mandibular tooth of the subject.

The upper and lower portions are engageable such that the portions maintain a restricted orientation relative to each other when engaged. The engaged restricted orientation maintains the mandible of the subject in the second or successive clinically beneficial orientation relative to the maxilla of the subject. Optionally, a series of clinically beneficial orientations are set at substantially the same time.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
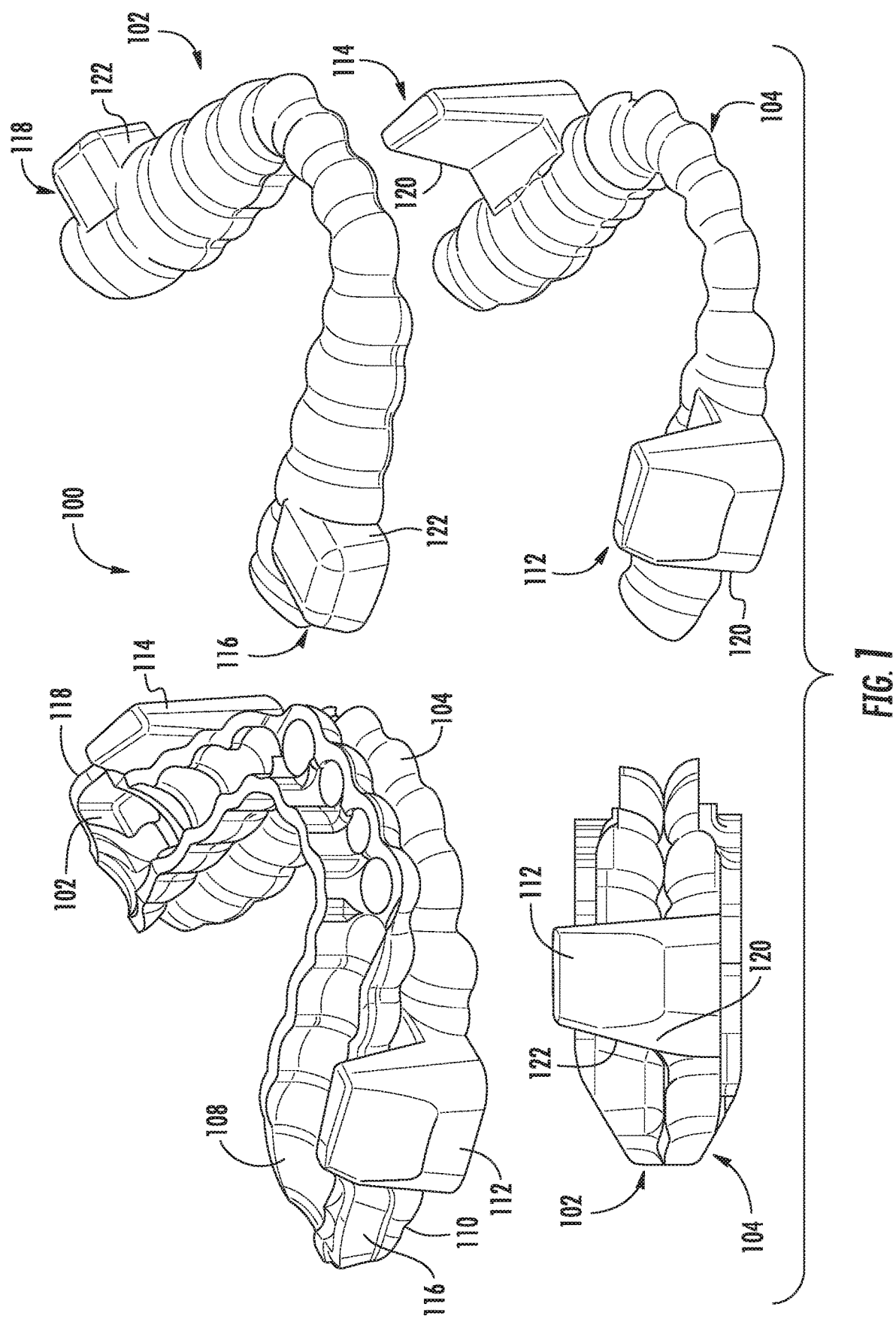
FIG. 1 is a schematic illustration of an upper portion and a lower portion of an example device for treatment of a sleep disorder or condition and of the example device engaged for treatment of a sleep disorder or condition.

Sleep disorders or conditions often cause significant morbidity and mortality including excessive daytime sleepiness, headache, depression, irritability, cognitive impairments, and other health problems.

For example, sleep apnea, including central sleep apnea and obstructive sleep apnea (OSA), is a common disease that carries significant risks for cardiovascular disease, mortality, and economic costs. The disorder arises during sleep when the victim undergoes repeated cessation of breathing. This cessation results from an obstruction of the throat air passage (pharynx) due to severe narrowing or a collapse of the throat air passage.

Repeated cessation of breathing reduces blood oxygen and disturbs sleep. Reduction in blood oxygen can cause hypertension, heart attacks and strokes. Additionally, sleep disturbances can produce excessive daytime sleepiness, headache, depression, irritability and cognitive impairments. Snoring and high upper airway resistance can create similar morbidity and mortality.

Standard treatment for OSA, continuous positive airway pressure (CPAP), entails the use of a mask to deliver positive air pressure that dilates the pharynx and eliminates obstruction. This therapy may be efficacious, but it is cumbersome and its effectiveness is compromised by a relatively low adherence rate, particularly in subjects with disease of mild and moderate severity. In current practice, CPAP adherence rate appears to approximate 50%.

The only currently available alternatives to CPAP are oral appliance therapy, surgery and life style modifications. Oral appliances maintain patency of the airway during sleep by stabilizing and protruding the mandible and/or the tongue. The most commonly used type of oral appliance is a custom-made mandibular repositioner (MR) which repositions the mandible. In clinical practice, a specialist dentist, working with a dental laboratory, fabricates a custom-fitted appliance encapsulating the upper and mandibular teeth. The appliance is then empirically adjusted to progressively reposition the mandible until a therapeutic end-point, at which apneas and hypopneas are eliminated, is reached. MR therapy is well accepted by most subjects but is not uniformly effective in eliminating sleep apnea. Reported effectiveness ranges from 50 to 65 percent of the subject population.

Candidates for MR therapy are typically selected based on predictive criteria with accuracy insufficient for clinical practice (eg BMI; neck circumference, severity of sleep apnea; characteristics of pharyngeal anatomy, facial bone characteristics); or on demonstrated effectiveness of the therapy through use of an oral appliance. Alternatively, oral appliance therapy can be recommended by prospectively demonstrating effectiveness using an oral appliance titration.

Studies of the passive pharynx indicate that the response of the pharynx to mandibular protrusion is "dose dependent;" incremental mandibular protrusion produces corresponding pharyngeal enlargement. Clinical experience, however, shows that excessive mandibular protrusion is undesirable, producing side effects such as pain and tooth movement that lead to discontinuation of therapy. Current practice is for a dentist to progressively protrude and/or alter other aspects of the relative position of the mandible until a symptomatic response occurs, and then reassess the subject by a sleep test to determine if OSA has resolved. This method allows for a crude titration that requires repeated visits to the dentist, and fabrication of an oral appliance in advance of knowing whether it will be effective for the subject. However, the position at which reassessment occurs depends upon patient report. It is of uncertain accuracy and may be influenced by a placebo effect.

Oral appliances are often designed so that the protrusive setting and sometimes the vertical setting and/or lateral setting can be adjusted by the subject or the treating dentist. Adjustment is provided by screw mechanisms, replaceable bite pads, and/or repositioned connectors such as elastics. Adjustment is necessary to titrate the subject to an effective therapeutic setting and is performed by the dentist with feedback from the subject to find the preferred therapeutic setting. Adjustment is also sometimes used to progressively reach a target setting in a gradual step wise manner as prescribed by the treating dentist so as to habituate the subject to the treatment. The mechanisms required to provide this fine adjustment adds significant cost to the fabrication of the appliance and restrict the adjustability to one or two directions. Various sized appliances can be used to titrate the appropriate geometry that is to be used. While this eliminates the cost of an adjustability mechanism, there is unnecessary cost in the multitude of appliances created as well as limitation to the resolution of the titration that is possible.

Moreover, while prior dental appliances have proven effective in maintaining the mandible in a protruded position to improve airway patency, they often result in undesirable side effects. One of the most common side effects is tooth movement and bite changes that can compromise chewing, comfort and facial appearance. Protrusion of the mandible during sleep can also cause pain in the region of the temporomandibular joint related to the stretching of jaw muscles and ligaments. Temporomandibular joint symptoms have been associated with a wide variety of physical ailments, including migraine headaches. Accordingly, uncertainty regarding a target therapeutic protrusive position means that many individuals suffering from sleep apnea and snoring disorders receive excessive mandibular protrusion and, as a result, are not able to tolerate existing dental appliances for long periods of time. Existing dental appliances also have limited adjustability in a maximum of one or two or three fixed directions, and cannot accommodate the unique requirements of each subject.

Provided herein are oral appliances that are optionally custom manufactured according to previously determined anatomical and therapeutic specifications. These devices provide a customized fit and attachment to the subject's dentition as well as provide a specific spatial relationship of the maxilla and mandible in space.

The prescribed geometry is based on a predetermined clinically beneficial orientation. The prescribed geometry may then be supplied to a manufacturer for fabrication of the appliance. The result is an oral appliance that positions the subject's mandible in any 3D orientation relative to the subject's maxilla such that therapy and comfort are achieved.

Referring to FIGS. 1-4, provided are oral appliances for treatment of a sleep disorder or condition in a subject. An example oral appliance 100 includes an upper portion 102 configured to receive at least one maxillary tooth of the subject and a lower portion 104 configured to receive at least one mandibular tooth of the subject.

The upper 102 and lower 104 portions are engageable, as shown in FIGS. 1-4, such that the portions maintain a restricted orientation relative to each other when engaged. A restricted orientation restricts movement of the upper 102 and lower 104 portions relative to each other in at least one degree of freedom.

The engaged restricted orientation is configured to maintain the mandible of the subject in a predetermined clinically beneficial orientation relative to the maxilla. A predetermined clinically beneficial orientation is an orientation of the mandible relative to the maxilla that reduces or eliminates at least one symptom or manifestation of a sleep disorder or condition. The sleep disorder or condition may include sleep apnea, obstructive sleep apnea, central sleep apnea, high upper airway resistance and/or snoring. Optionally, the restricted orientation maintains a minimal level of repositioning of mandible relative to the maxilla in at least one degree of freedom. In some examples, the restricted orientation maintains a minimal level of repositioning of mandible relative to the maxilla in two, three, four, five or six degrees of freedom.

Therefore, the oral appliances can be manufactured to a prospectively determined prescribed geometry that results in a known position of the subject's mandible and a previously determined therapeutic effect. The known position of the subject's mandible and maxilla maintains the mandible of the subject in a predetermined clinically beneficial orientation relative to the maxilla of the subject. The prospectively determined prescribed geometry optionally considers one or all of: airway size and reduction of obstruction to airflow, improved oxygen saturation, snoring sound, minimization of side effects and subject comfort, which indicate the clinically beneficial orientation.

The clinically beneficial orientation can be determined in a number of ways. For example, several devices have been designed which can be used to determine and define a clinically beneficial position of the mandible relative to the maxilla. In one example, U.S. Pat. No. 7,832,403 describes a jig to adjust the horizontal and vertical position of the mandible in an awake subject to determine an optimal position of the mandible by visual inspection of the airway. In another example, pharyngometers, such described in U.S. Pat. No. 5,666,960, provide an analysis of airway obstruction and data with which to make adjustments in the subject's oral appliance. In yet another example, U.S. Patent Publication No. 2007-0068534 describes a bite jig in combination with a pharyngometer to determine the optimal position of the mandible to minimize restriction of airflow. In another example, U.S. Pat. No. 5,826,579 describes a remotely controlled device applied during polysomnography using temporary dental trays that adjust the mandibular protrusion until evidence of pharyngeal obstruction is eliminated or reduced and provides the minimum protrusive distance required to eliminate obstruction.

For example, in the case of sleep apnea, the clinically beneficial orientation can be determined by positioning of the mandible for the elimination or reduction of obstruction. This is optionally determined in a titration test, where the position of the mandible is adjusted while the subject is monitored based on feedback signals (e.g. airflow, O₂sat, sound). A desired airflow, such as one that reduces or eliminates one or more symptoms or manifestations of a sleep disorder or condition, may be provided as a set position that provides a therapeutic effect for the subject, or it may be provided as a therapeutic zone, or range of positions, within which the subject will be provided with a therapeutic treatment. The therapeutic zone may also be provided as a map that describes the effect of position other than to the optimal reposition on the subject's airway. The desired position for airflow that results from, and therefore can be used to indicate, the predetermined clinically beneficial orientation, are therefore optionally determined with the use of devices such as pharyngometers or devices that allow visual inspection of the subject's airway while they are awake or other methods to predict or measure airflow.

The clinically beneficial orientation may optionally be predetermined in a sleep test by use of a Remotely Controlled Mandibular Positioner (RCMP). An RCMP is used to obtain a data set representing the predetermined clinically beneficial orientation. For example, the RCMP is used to obtain the data set by fitting a temporary oral appliance to the subject's teeth and incrementally and reversibly advancing the subject's mandible anteriorly with respect to the maxilla while the subject is sleeping under full polysomnographic monitoring.

The RCMP is used to predetermine a clinically beneficial orientation of the mandible relative to the maxilla for a sleep disorder or condition where one or more symptom or manifestation of a given sleep disorder is reduced or eliminated.

The repositioning of the mandible pulls the tongue forward and increases available intraoral space for the tongue and increases the subject's airspace, thereby decreasing upper airway obstruction. Such obstruction can be a causative factor in obstructive sleep apnea and snoring. A titration device such as an RCMP can be used to titrate the optimal position of the jaw for removal of the obstruction. The RCMP can be used in the clinical setting by a technician to advance the mandible until the feedback signals (e.g. airflow and/or O2 saturation and/or snoring) indicate removal of the obstruction or in a remote or home setting using automated algorithms to adjust the position automatically based on feedback signals. These data can be used to establish a data set from when the mandible is in a clinically beneficial orientation relative to the maxilla. This data set and the clinically beneficial orientation, which the data set reflects, can be used to determine the restricted orientation that the device 100 will maintain in the subject to reduce or eliminate one or more symptom or manifestation of a sleep disorder or condition in a subject.

Figure 5:
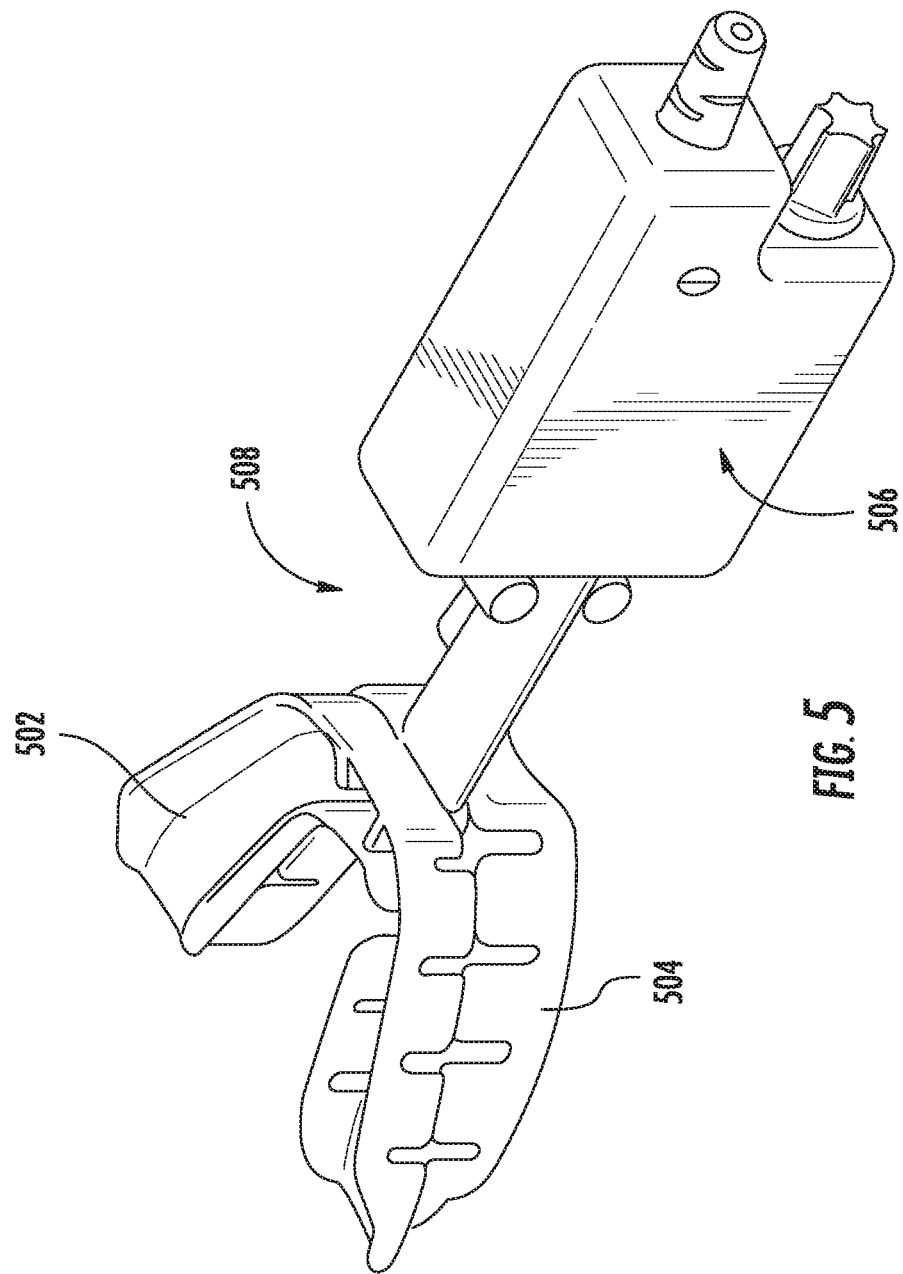
FIG. 5 is a schematic illustration of an example mandibular positioner and titration trays for an example remotely controlled mandibular positioner (RCMP) device.

As shown in FIG. 5, an example RCMP appliance 500 that may be used in the clinic by a technician to determine the clinically relevant position in one dimension (protrusion of the mandible along the anterior posterior direction) is provided.

Figure 6:
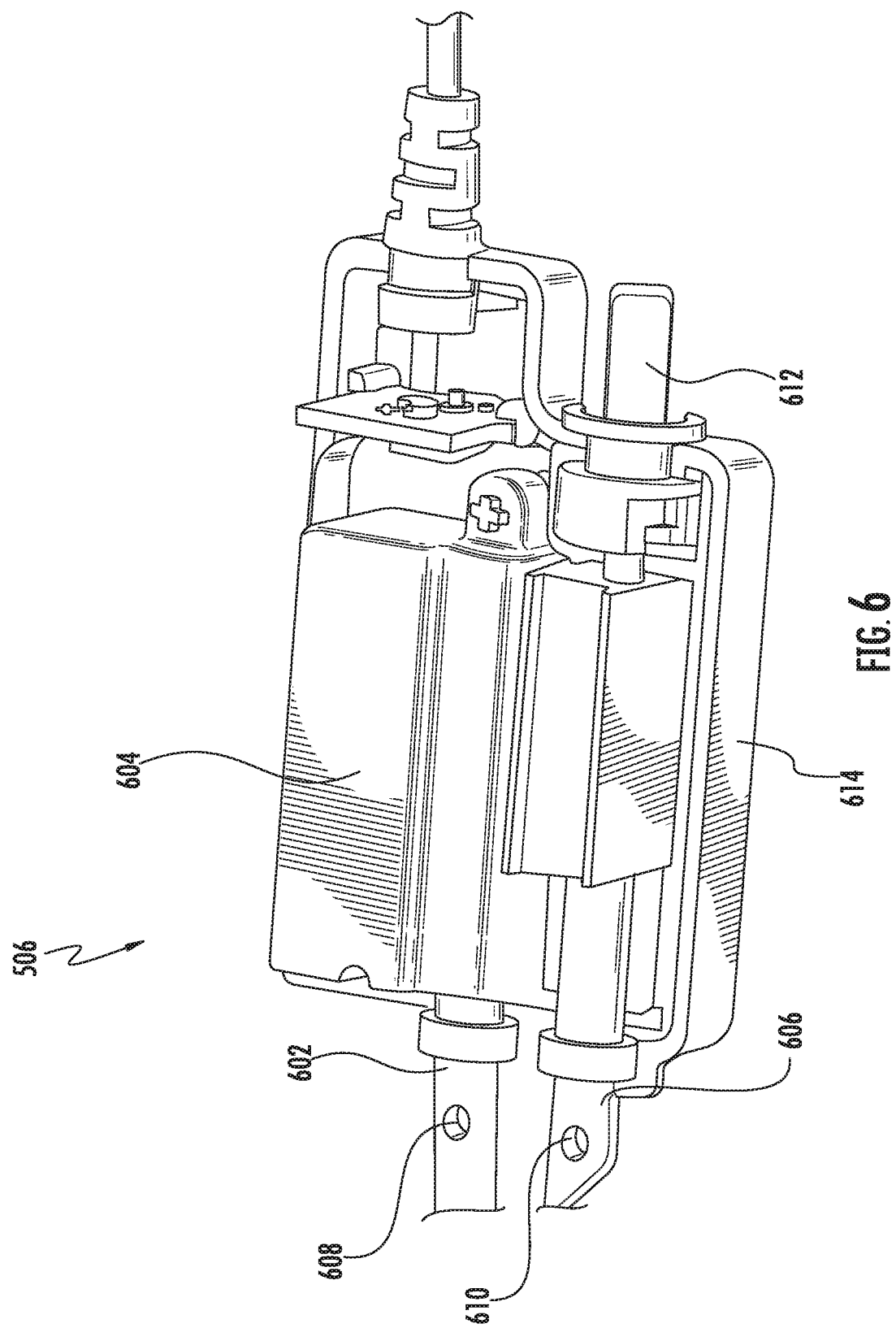
FIG. 6 is a schematic illustration of operative portions of an example mandibular positioner for use in the RCMP device of FIG. 5.

The example RCMP appliance 500 includes upper 502 and lower 504 disposable dental trays that are used to hold onto the teeth by means of a quick-set retention material. The titration trays 502 and 504 include a portion that extends out from the dental tray, the mounting bracket 508. The mounting bracket 508 includes: a rail guide system to constrain the motion in the anterior-posterior direction; a scale and pointers to measure the relative position of the trays; and an attachment system to firmly connect the titration trays to the mandibular positioner 506. The upper tray 502 attaches firmly to the linear actuator rod 602, as shown in FIG. 6; and the lower tray 504 attaches firmly to the manual adjustment rod 606, as also shown in FIG. 6, of the mandibular positioner 506.

The titration trays 502 and 504 are optionally limited in their movement to the anterior-posterior dimension in a single axis by the rail guide system. Rails extend from the lower tray 504 and the mounting bracket of the upper tray is threaded through the guide, such that the mounting brackets lie flush with one another. Lateral and cranial-caudal movement is optionally less than 5 mm at the molar end of the trays with the upper and lower trays aligned.

An 18 mm linear millimeter scale is optionally displayed on the upper surface of the upper mounting bracket. As shown in FIG. 6, the titration trays 502 and 504 attach to the mandibular positioner 506 via attachment points. The attachment point slides over the end of each rod (actuator or the manual adjustment rod) and aligns with a hole 608 in the linear actuator rod 602 or with a hole 610 in the manual adjustment rod 606. Pins are inserted into the holes of the upper and lower trays to provide a firm attachment to the mandibular positioner.

The trays 502 and 504 are able to slide smoothly against each other using the force of the linear actuator 604 and the manually adjustable rod 606 of the mandibular positioner 506. The titration trays (which include the dental trays and mounting brackets) are optionally manufactured by standard injection molding processes.

The mandibular positioner 506 retracts and extends a rod 602 to adjust the tray positioning by means of a small force linear actuator 604. The mandibular positioner attaches to the titration trays and adjusts their relative position by movement of the linear actuator. The mandibular positioner 506 consists of the linear actuator and rod 602; a manually adjustable rod 610 that is extended or retracted manually by a knob mechanism 612; a molded housing 614 and seals that limit any fluids or secretions from entering the housing 614.

By extending the linear actuator rod 602 attached to the upper tray 502, the RCMP pushes on the maxillary teeth and pulls on the mandibular teeth, thus displacing the jaw. RCMP software interacts with a polysomnographic computer and allows a technician to control fine adjustments of the relative position of the mandible.

Optionally, the linear actuator 604 is a complete, self contained linear motion device with position feedback. For example, a model PQ12, 63:1 linear actuator from Firgelli Technologies Inc., Victoria, Canada may be used. This example actuator can be operated with low voltage (12 Vdc or less).

The linear actuator rod 602 is extendable and retractable in the anterior-posterior dimension. The rod is capable of being extended 12 mm more than its position when flush with the housing (i.e., fully retracted). The linear actuator rod 602 is controlled by software that may be housed on a remote computing device 706.

The manually adjustable rod 606 is controlled by the technician using a manual knob 612; and can be extended and retracted in the anterior-posterior dimension. It is capable of being extended 10 mm more than its position when flushed with the housing (i.e., fully retracted). The linear actuator 604 and manually adjustable rods 606 pass through custom droplet-tight seals that are secured in the front wall of the mandibular positioner housing 614.

The linear actuator rod is optionally made of acetal copolymer and is not in contact with the subject. The manual adjustment rod 606 and knob 612 is manufactured by injection molding and is also optionally made from acetal copolymer and is not in contact with the subject.

The housing 614 is designed to prevent fluids from entering and contacting the actuator 604. The mandibular positioner 506 is sealed such that end users cannot take the housing apart. The housing is optionally manufactured by injection molding in two parts which are assembled with cyanoacrylate adhesive.

The controller 704 includes the circuitry that controls the linear actuator 604 and the cabling between the controller and the mandibular positioner 506 and the controller 704 and the PSG computer 706. The controller 704 interfaces with the PSG workstation computer 706 and with the mandibular positioner 506. It optionally comprises a single circuit board that is connected to the computer 706 through USB 2.0 and to the mandibular positioner 506 over a cable. The controller 704 is optionally responsible for controlling the motor and sensing the position. The linear actuator is controlled in relation to an analog input voltage and outputs the position feedback signal as an analog voltage. The PSG computer software has a simple interface to set or query the current displacement. The controller also includes hardware extensions to interface with the PSG for position information.

The controller comprises a microcontroller, such as a model LM3S3748 microcontroller from Texas Instruments, Inc, (Dallas, Tex.). This part provides an ARM Cortex-M3 core with built in USB and a 10-bit multichannel ADC.

Power is optionally provided by a 5V-2 A medical grade (double insulated) wall power supply 714 connected with a standard barrel power jack. The independent power supply is UL marked and approved. A power switch on the front face of the controller powers the device on and off.

The controller may also be connected to a polysomnogram (PSG) which will display a signal proportional to the current position of the mandibular positioner. A 12-bit I2C connected digital to analogue converter is used to provide this signal which will be in the range of 0V to 1.0V, meeting the output requirements of the targeted PSG's.

Figure 7:
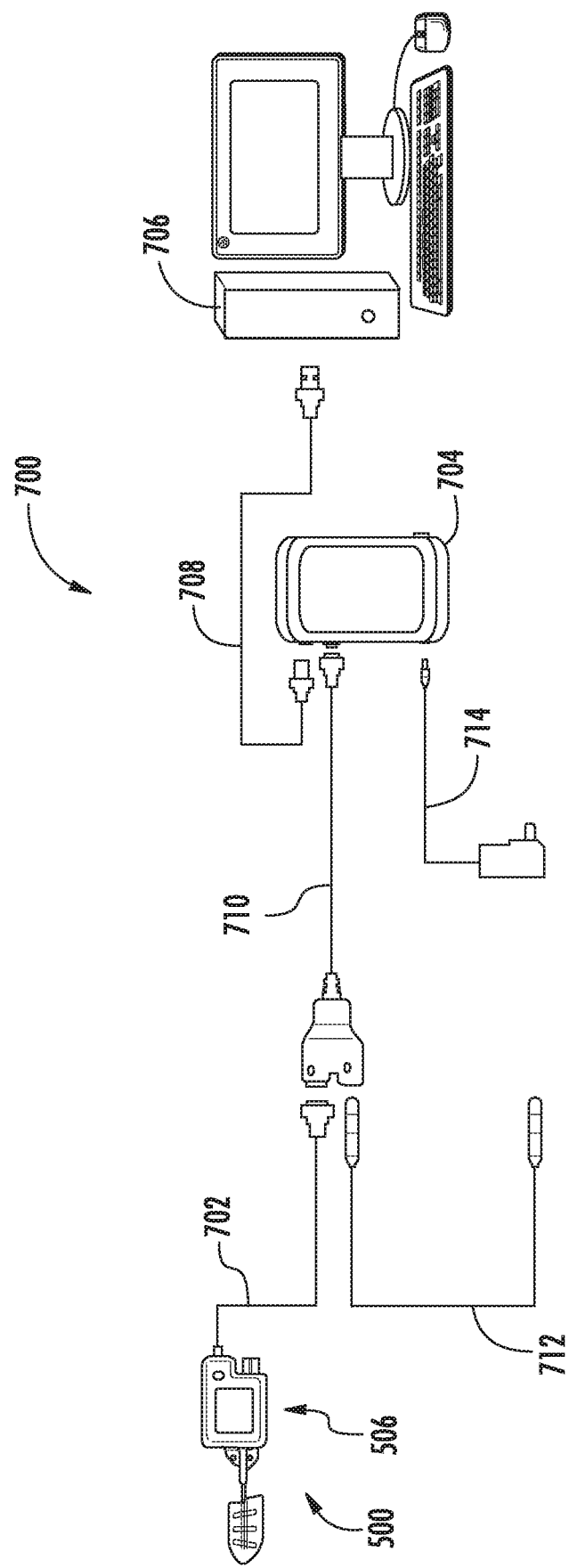
FIG. 7 is a schematic illustration of a RCMP system.

The RCMP system 700 optionally consists of four cables. A layout of the cable connections to the specific components are provided in FIG. 7. Cable 708 is the cable from the PC to the controller module. It is optionally a standard, off the shelf USB 2.0 cable, 6 feet in length with a USB type A connector on one end, and a USB type B connector on the other end.

Cable 710 is the cable from the controller box to a "Y" connector. It is 50 feet in length with the capability of joining to an additional cable of 50 feet for a total of 100 feet in length.

Cable 702 is the cable from the "Y" connector to the mandibular positioner 506. It is a light, flexible, 10 feet in length, with appropriate strain relief. It is a five conductor shielded cable, operating at low voltage. The connection to the "Y" connector is the same connector type as the Controller Cable connection to the controller.

Cable 712 is the cable from the "Y" connector to the PSG. It is a standard, off the shelf, mono cable with 3.5 mm stereo jacks on each end and is 10 feet in length.

The RCMP device 500 and system 700 may be used to determine a clinically beneficial orientation while the subject is under full polysomnographic cardio-respiratory monitoring. In these cases, the technician monitors the respiratory air flow and the oxyhemoglobin saturation of the subject during an apnea or snoring and titrates the position of the mandible to reestablish normal flow, or to reduce one or more symptom or manifestation of the apnea or snoring.

The oral appliances used with the RCMP optionally comprise customized, temporary dental trays filled with dental impression material. The trays 502 and 504 are fit to the teeth by a professional and inserted for the duration of the test to grip the teeth to facilitate movement of the mandible. The trays 502 and 504 allow movement of the jaw in the occlusal plane along the anterior-posterior axis.

The RCMP 500 adjusts the mandible in fine increments while the technician observes the immediate cardio-respiratory response in all stages of sleep and body positions. Thus, the RCMP allows the technician to adjust the protrusive position of the mandible while the subject is sleeping with full polysomnogram monitoring. Changes in airflow and $O_2$sat are used to establish a protrusive setting that at least partially defines the clinically beneficial orientation by reducing at least one symptom or manifestation of a sleep disorder or condition.

In addition, the clinically beneficial orientation can be determined by repositioning the mandible relative to the maxilla in other ways, such as adjusting the amount of bite opening and/or separation of the teeth to further improve the airflow. For multidimensional titration of airflow, an RCMP may be used where the position of the mandible is titrated in multiple degrees of freedom. In addition to the adjusting the protrusion, the position may be adjusted for the separation between the occlusal surfaces of the teeth, and may also adjust the amount of bite opening. In these instances the therapeutic position, or clinically beneficial orientation, is optionally described in multiple variables and the therapeutic zone, including the clinically beneficial orientation is optionally provided as a three dimensional map.

In addition, the clinically beneficial orientation can be determined by an automated version of the RCMP which repositions the mandible relative to the maxilla in response to changes in the airflow and/or oxygen saturation. The automated RCMP can be used in the presence of a technician who monitors the adjustment and intervenes if necessary, or unattended, for instance in the home environment of the patient. The auto RCMP includes algorithms that identify respiratory disturbances and/or evaluates changes in airflow caused by changes in mandibular position.

The oral appliances are optionally fabricated according to the subject's unique requirements with regards to airflow, other dental issues and comfort. These unique requirements are prospectively determined and form the prescribed geometry that is indicative of the clinically beneficial orientation.

The prospectively determined clinically beneficial orientation is optionally provided to an appliance manufacturer for fabrication based on the clinically beneficial orientation or to a professional such as a dentist. If supplied to the professional, they may choose to make further adjustments to the prescribed position. For instance, they may choose to adjust the separation of the occlusal planes of the teeth to minimize the force on the temporal mandibular joint.

A variety of technologies (tensing etc.) are also optionally used to further assess the clinically beneficial orientation for the oral appliance in the dental office setting. These assessments will result in further adjustments to the clinically beneficial orientation that are optionally based on, for example, subject comfort, dental considerations such as tooth movement, or reduction, including minimization, of forces for temporal mandibular joint issues. Alternatively, adjustments may be made by the professional's own judgement and experience. The adjustments made by the professional may be made in all six degrees of freedom of the mandibular joint. The adjustments may be made with the use of a jig where one or more or all of the adjustments can be applied at once with the original clinically beneficial orientation, and where the effect of the adjusted position can be assessed and measured directly on the patient. These adjustments may be alternatively be made to the clinically beneficial orientation automatically by the use of a computer program, or by manually adjusting the data set of the clinically beneficial orientation. Some combination of two or all of these methods may also be used. The resulting adjusted clinically beneficial orientation is recorded as a data set, is registered and is used to manufacture the device.

Optionally, the upper 102 and lower 104 portions of the oral appliance device 100 have a fixed predetermined geometry. The fixed predetermined geometry of the upper 102 and lower 104 portions function to position the mandible of the subject in the predetermined clinically beneficial orientation relative to the maxilla when the upper and lower portions are engaged.

The upper 102 and lower 104 portions are engageable such that the portions maintain a restricted orientation relative to each other when engaged. The engaged restricted orientation is configured to maintain a minimal level of repositioning of mandible relative to the maxilla in at least one degree of freedom. Optionally, the restricted orientation maintains a minimal level of repositioning of the mandible relative to the maxilla in two, three, four, five or six degrees of freedom.

The fixed predetermined geometry of the upper and lower portions are optionally based on a data set obtained from the subject when the mandible of the subject is positioned into the clinically beneficial orientation relative to the maxilla, for example by using the methods described above. The data set is optionally obtained while the subject is sleeping. For example, as described above, with the use of an RCMP. As also described above, whether or not the subject is sleeping, the data set may be obtained with the use of a titration device, such as used with a RCMP.

A coordinate system that relates the position of the mandible relative to the maxilla is optionally used to describe the clinically beneficial orientation and to manufacture a device where the engaged restricted orientation maintains the clinically beneficial orientation.

For one dimensional repositioning, such as mandibular protrusion, a reference point may be used from which mandibular displacement is measured. As an example, this may be the end to end position of the incisors. Alternatively, full retrusion or protrusion of the mandible may be used as a zero point.

For two or three dimensional repositioning including protrusion, separation of the occlusal planes, and bite opening, a two dimensional coordinate system is used. If additional dimensions are considered, lateral displacements, or tilting or twisting of the jaw, a three dimensional coordinate system is optionally used.

Figure 8B:
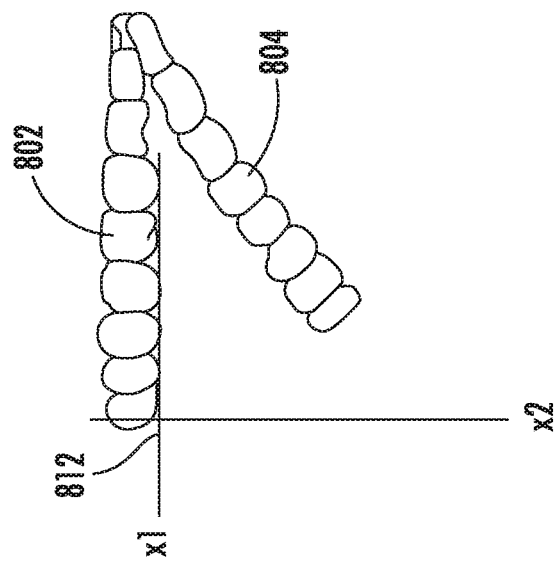
FIGS. 8A and 8B are schematic illustrations showing an example coordinate system for creating a device for treating a sleep disorder or condition.
Figure 8A:
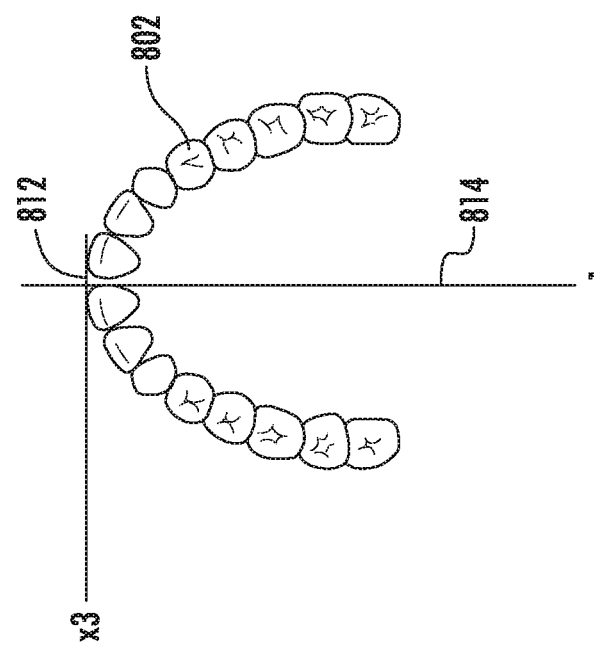

As shown in FIGS. 8A and 8B, an example two (x1,x2) or three (x1,x2,x3) dimensional coordinate system can be established from identifiable features of the jaw and teeth. In FIGS. 8A and 8B, it is shown that the occlusal plane of the maxillary teeth 802 and the inter-incisal space of the upper (maxilla) incisors 812 can be used. The x1 axis resides in the occlusal plane of the maxillary teeth 802 and intersects the inter-incisal point of the incisors 812 and the midline 814 of the maxillary teeth. The x2 axis is then positioned perpendicular to the occlusal plane, and intersects x1 at the inter-incisal space of the upper incisors 812. The third axis (x3) is positioned perpendicular to the line x1, in the occlusal plane, and also intersects at 812. This coordinate system is optionally used to describe the mandible with respect to the maxilla in up to six dimensions.

In two dimensions, the mandible is optionally described by a line and a reference point. An example reference point is the inter-incisal space of the incisors 812, and the line defined by this point and the midline of the mandibular teeth 804 (again, at the occlusal surface). In three dimensions, the mandible is optionally described by the line 814, the point 812 and the occlusal plane.

The coordinate system is used to describe the clinically beneficial orientation of the mandible relative to the maxilla.

The relative position may be measured by a gauge, directly from a titration appliance, such as an RCMP or from an image of the jaw. The coordinate system is also used to manufacture an appliance that can accurately maintain the position of the mandible in the desired orientation.

As shown in FIG. 1-4, the upper portion 102 of the device optionally comprises an upper tray 108 configured to house one or more teeth of the subject and the lower portion 104 optionally comprises a lower tray 110 configured to house one or more teeth of the subject. Optionally, the upper tray 108 has a geometry configured to communicate with a plurality of the maxillary teeth of the subject and wherein said geometry is at least partially based on a digital scan of the maxillary teeth. Optionally, the lower tray 110 has a geometry configured to communicate with a plurality of the mandibular teeth of the subject and wherein said geometry is at least partially based on a digital scan of the mandibular teeth.

For manufacturing the upper and lower trays a mold or a scan of the subject's teeth or mouth tissue is optionally acquired. For example, casts of the subject's teeth and gums may be taken. Wax bites, direct contact scanning, x-ray imaging, tomographic imaging, sonographic imaging, and other techniques for obtaining information about the position and structure of the teeth, jaws, gums and other orthodontically relevant tissue may also be used.

The arrangement of the subject's teeth and other tissues required for the purpose of fitting the upper and lower trays may be combined with the dataset describing the predetermined clinical orientation to manufacture the device. This may be optionally derived using traditional techniques of combining dental impressions with bite registrations such as those created using wax bites or impression materials as described above, obtained while the mandible and the maxilla are placed in the clinically beneficial orientation. Alternatively, these could be combined in one step, for example, utilizing a jig fitted with impression material that is used to recreate the predetermined clinically beneficial orientation and simultaneously record the bite registration and dental anatomy.

Alternatively, manufacturing the 3D positioning of the upper 102 and lower 104 portions is optionally accomplished with a digital data set that may be optionally derived from a dental scan and the clinically beneficial orientation. The digital scan and the resulting anatomy and geometry are optionally provided as a digital image format (CAD) for manufacture of the upper and lower portions and/or the connector. The scans may be collected with a common reference point if the position of the jaw is fixed during the scanning. If the scans are independently collected (ie without a common reference point) the scans may be combined according to a common coordinate system, for example, using the coordinate system described above. The model of the maxillary teeth 802 is created with reference to this coordinate system. A model of the mandibular teeth 804 is created with reference to a local coordinate system established by the same principles (occlusal plane and interdental space of the lower incisors). The two models are combined according to the dataset of the clinically beneficial position.

The digital scan is optionally combined with the digital data set describing the clinically beneficial position using common reference points. For example, the subject may be placed in the clinically beneficial position and one, two, three or more reference points on the upper and mandibular teeth may be recorded by the use of common coordinate system. A digital scan of the upper and mandibular teeth may then be independently obtained, and the same reference points identified. The digital scans may then be arranged in two or three dimensions according the coordinates of the reference points in the clinically beneficial orientation to create a three dimensional model of the jaw in the clinically beneficial orientation.

The model is then used to calculate the geometry of the engaged restricted orientation of the appliance required to maintain the position of the mandible relative to the maxilla. The complete digital data set may then be provided for the purpose of manufacturing of a device, such as an oral appliance as described herein or a device, or portions of a device.

The complete digital data set may be used to create a mold of a positive impression of upper and lower trays from which an appliance may be manufactured. Alternatively, the complete digital data set may be used to directly manufacture an appliance. Alternatively, the data set of the digital scan of the upper and lower teeth may be used to manufacture a device, or portions of a device, such as trays, that are connectable with a titration device for the purpose of obtaining the clinically beneficial position. The clinically beneficial position is then combined with the digital scan to obtain the complete digital data set that may be used to manufacture the appliance.

The manufacturing technique is optionally common thermo plastic manufacturing techniques, such as injection molding and thermo forming; and rapid manufacturing techniques such as SLA and SLE (stereolithography) which use plastic compounds in conjunction with laser technology or three-dimensional printing technology such as fused filament fabrication (FFF) which is an additive technology where plastic is deposited in layers by a computer-controlled nozzle to rapidly produce devices. This manufacturing method allows for customized repositioning of the mandible, allowing for asymmetry of jaw, unilateral pain etc to be dealt with.

The digital data set may be transmitted to an offsite location where the appliance is manufactured and then shipped to the dentist or other professional and provided to the patient. Alternatively, the dentist or professional may manufacture the appliance directly in his office, for instance with three-dimensional printing technology, and provide the appliance to the patient during the same visit. This manufacturing method allows a dentist or other professional to treat a patient with a custom fit appliance set at a patient's clinically beneficial position on the night following a titration test.

The restricted orientation optionally maintains a minimal level of repositioning of mandible relative to the maxilla in at least one degree of freedom. In some examples, the restricted orientation maintains a minimal level of repositioning of mandible relative to the maxilla in two, three, four, five or six degrees of freedom.

The device can be used to alter and maintain the protrusive distance of the mandible (translation of the mandible relative to the maxilla in the anterior posterior direction). Protrusion of the mandible lengthens anterior pharyngeal muscles and tends to open the pharynx.

The device can be used to alter and maintain the bite opening of the subject, which is a rotational movement of the mandible around the condyle which opens the bite and displaces the mandible posteriorly and caudally. This has implications for the treatment of sleep apnea as a number of pharyngeal muscles, eg, genioglossus, geniohyoid, stylosglossus, either directly or indirectly attach to this anterior region of the mandible. The effects of the mandible's rotation on the mechanics of the passive pharynx demonstrate that rotation increases closing pressure and reduces maximum cross-sectional area of the airway.

While the temporomandibular joint has two primary movements, translation (protrusion) and rotation, a smaller form of vertical adjustment is also optionally used. Parallel separation, i.e. caudal movement of the condyle in the absence of translation is limited (1 to 3 mm) and a small separation of the T-M joint surface represents the normal, unloaded condition of the joint. Thus, in the mandibular protruded situation, the joint surfaces should be separated. This is particularly important during long term position or bruxism, when loading of the joint by apposition of the surfaces may cause pain and produce joint deterioration. This movement provides additional space for the tongue. Therefore, position in any of these three dimensions (protrusion, bite opening, parallel separation) each have therapeutic effect and may be independently considered in determining the predetermined clinically beneficial orientation.

The engaged restricted orientation may maintain a minimal level of mandibular protrusion in the subject. The minimal level of protrusion is optionally at least 1.0 mm or greater. The minimal level of protrusion may orient the mandible and maxilla of the subject such that at least one symptom or manifestation of the sleep disorder or condition is reduced or eliminated when the device is used in the subject.

In addition, or independent to, maintaining a minimal level of mandibular protrusion, the restricted orientation may optionally maintain a minimal level of bite opening in the subject. Optionally, the minimal level of bite opening is at least 0.5 degrees or greater. The minimal level of bite opening alone, or in combination with the minimal level of mandibular protrusion, orients the mandible and maxilla of the subject such that at least one symptom or manifestation of the sleep disorder or condition is reduced or eliminated when the device is used in the subject.

In addition, or independent to, maintaining a minimal level of mandibular protrusion and/or a minimal level of bite opening the restricted orientation may optionally maintain a minimal level of occlusal plane separation in the subject. Optionally, the minimal level of occlusal plane separation is at least 1.0 mm or greater. The minimal level of occlusal plane separation alone, or in combination with either or both the minimal level of mandibular protrusion and bite opening, orients the mandible and maxilla of the subject such that at least one symptom or manifestation of the sleep disorder or condition is reduced or eliminated when the device is used in the subject.

The minimal levels of protrusion, bite opening, and/or occlusal plane separation can be used to define a therapeutic zone. A therapeutic zone represents a range of positions, within which the subject is provided with a therapeutic treatment.

Again referring to FIGS. 1-4, the example device 100 may further comprise one or more connector. Optionally, as shown in FIG. 1, the connector has a right 118 and left 116 maxillary portions and right 114 and left 112 mandibular portions. The connector is optionally configured to connect the upper and lower portions to position the mandible of the subject in the predetermined clinically beneficial orientation relative to the maxilla when the upper and lower portions are engaged.

Optionally, the connector has a fixed predetermined geometry. The fixed predetermined geometry of the connector is optionally based on a data set obtained from the subject when the mandible of the subject is positioned into the clinically beneficial orientation relative to the maxilla, as described above.

A dentist or other professional may select the style of connector based on various factors, in order to put a patient in a clinically beneficial position. A choice by a dentist or other professional optionally varies based on the patient's preference, mode of airflow during sleep (i.e., nasal or oral breathing), age, sex, condition, degree of protrusion, and the presence of other disorders such as temporomandibular joint issues or bruxism. A connector may be chosen to provide a therapeutic or clinically beneficial position.

Other factors that a dentist or other professional may consider in selecting a connector include the disorder being treated and the severity of the disorder; the time of administration or treatment; the method of administration of treatment; the duration of the treatment; and like factors well known in the medical and dental arts. The treatment or connector can be adjusted by the individual dental professional in the event of any counterindications.

The right and left mandibular connector portions may include surfaces 120 that can seat against surfaces 122 of the right and left maxillary connector portions. When the surfaces seat against each other, the upper and lower portions are connected such that the predetermined clinically relevant beneficial orientation is maintained.

Figure 2:
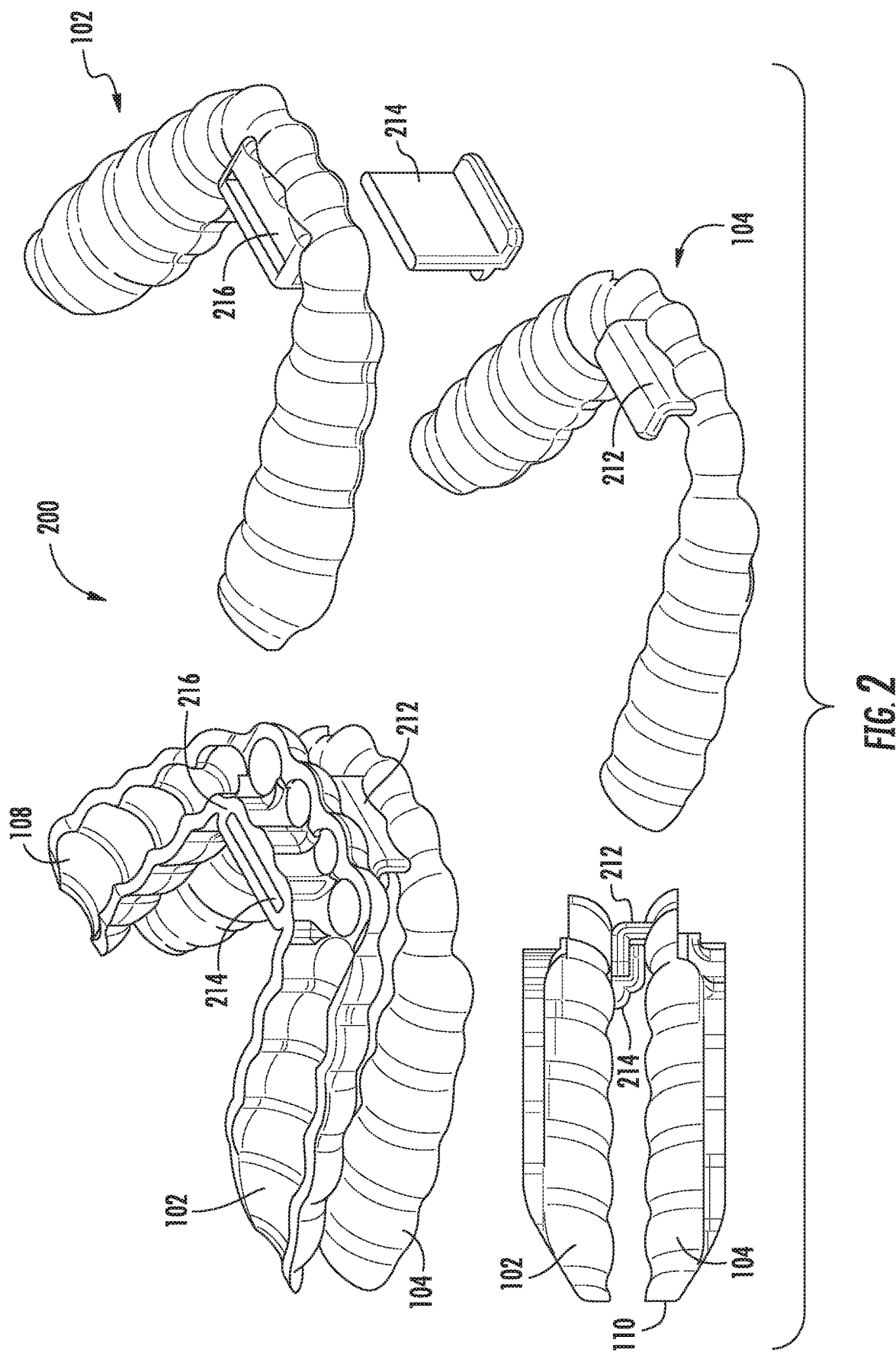
FIG. 2 is a schematic illustration of an upper portion and a lower portion of an example device for treatment of a sleep disorder or condition and of the example device engaged for treatment of a sleep disorder or condition.

Referring to FIG. 2, the example device 200 may further comprise one or more connector. Optionally, the connector has one or more maxillary portion 216 and one or more mandibular portion 212. These may be located centrally as in the figure, or multiple connectors located on the right and left side. The connector, either one or both of 212 and 216, is optionally configured to connect the upper and lower portions to position the mandible of the subject in the predetermined clinically beneficial orientation relative to the maxilla when the upper and lower portions are engaged by use of an adjustable stop 214. Optionally, the adjustable stop 214 is optionally configured to connect the upper and lower portions in the clinically beneficial position.

Figure 3:
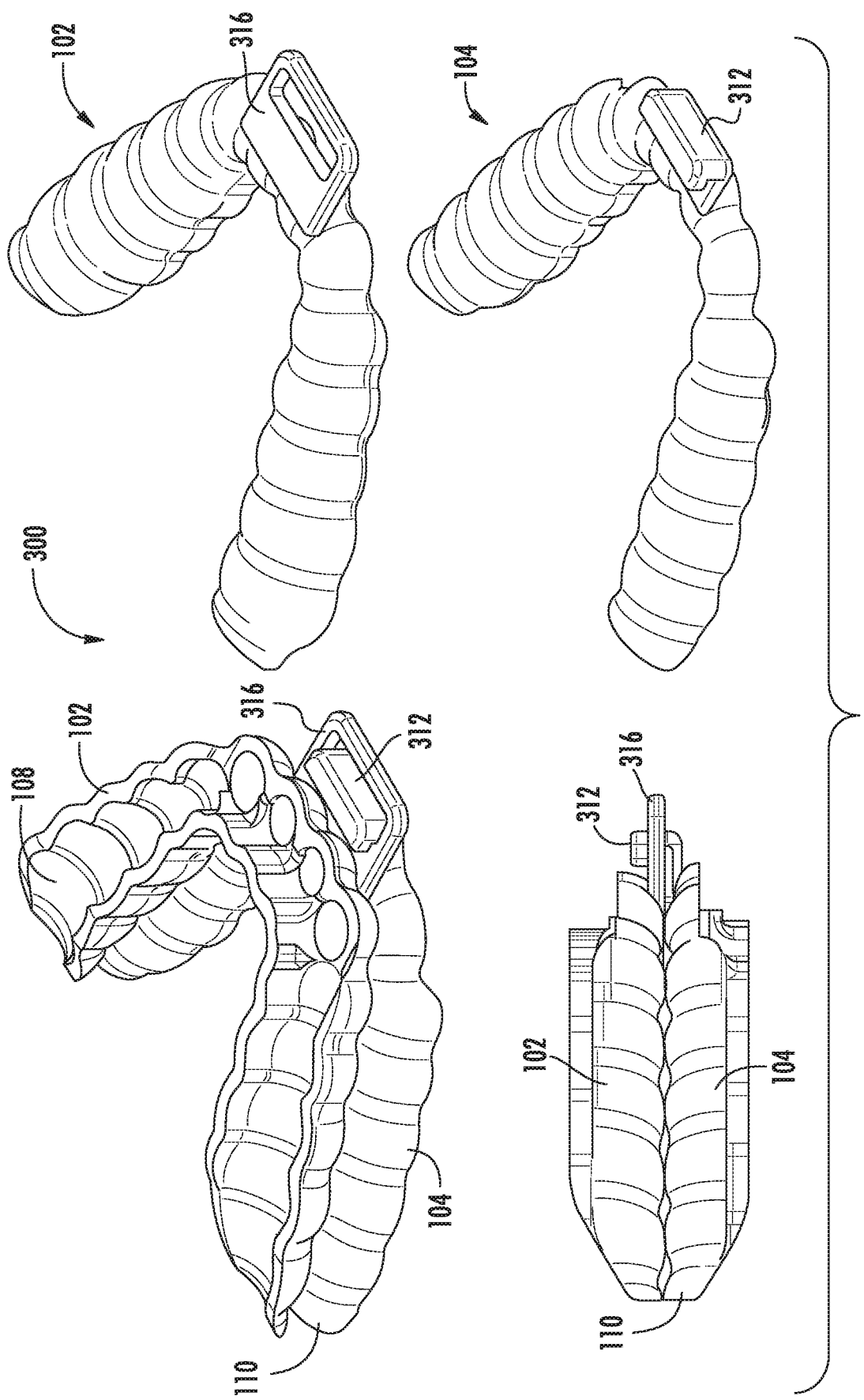
FIG. 3 is a schematic illustration of an upper portion and lower portion of an example device for treatment of a sleep disorder or condition and of the example device engaged for treatment of a sleep disorder or condition.

Referring to FIG. 3, the example device 300 may further comprise one or more connector. Optionally, the connector has one or more maxillary portion 316 and one or more mandibular portion 312. These may be located centrally as in the figure, or multiple connectors located on the right and left side. The connector, either one or both of 312 and 316, is optionally configured to connect the upper and lower portions to position the mandible of the subject in the predetermined clinically beneficial orientation relative to the maxilla when the upper and lower portions are engaged by one of 312 or 316 inserting one inside the other.

Figure 4:
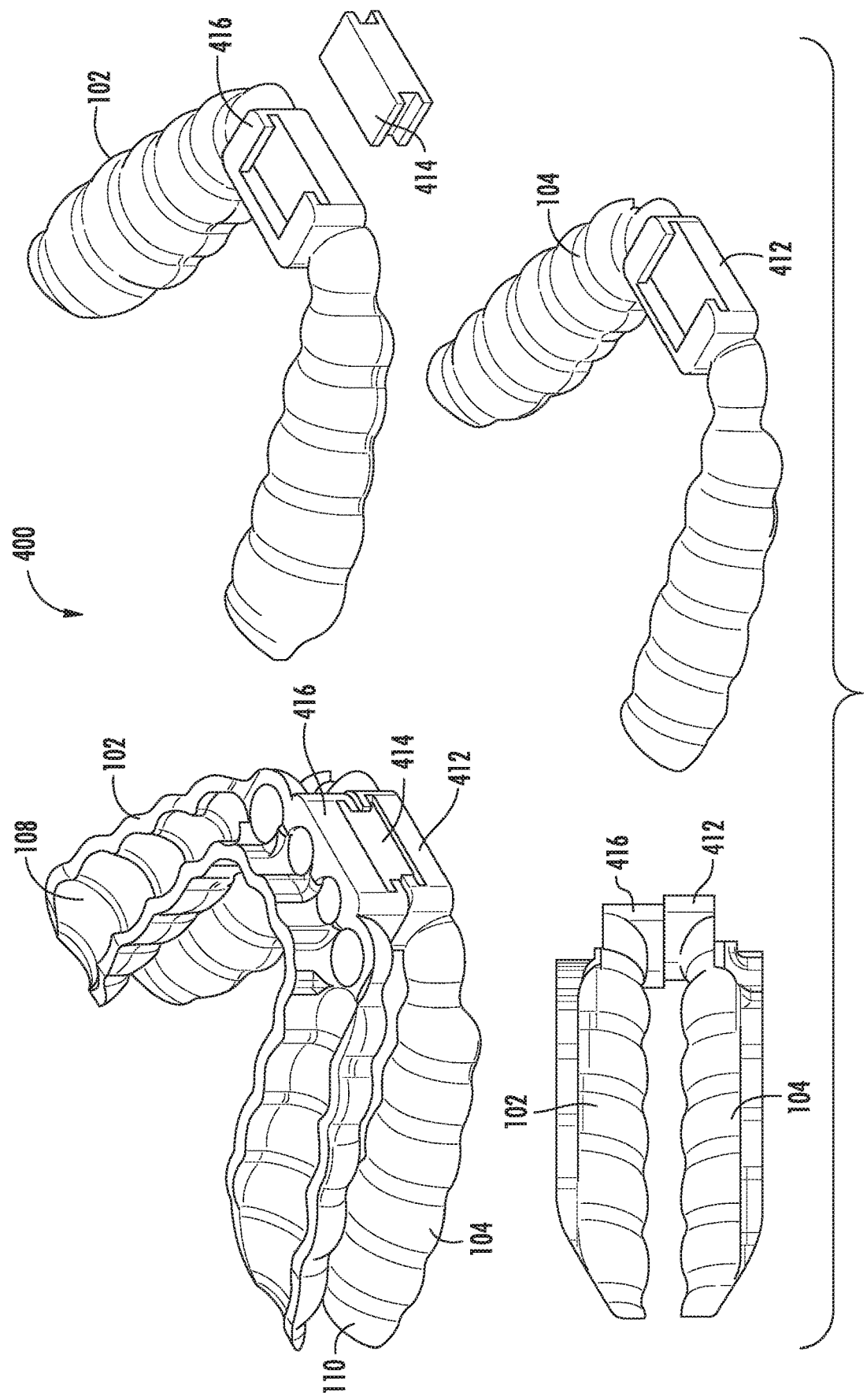
FIG. 4 is a schematic illustration of an upper portion and lower portion of an example device for treatment of a sleep disorder or condition and of the example device engaged for treatment of a sleep disorder or condition.

FIG. 4 provides an alternative example to the device described in FIG. 2, where the example device 400 may further comprise one or more connector. Optionally, the connector has one or more maxillary portion 416 and one or more mandibular portion 412. These may be located centrally as in the figure, or multiple connectors located on the right and left side. The connector, either one or both of 412 and 416, is optionally configured to connect the upper and lower portions to position the mandible of the subject in the predetermined clinically beneficial orientation relative to the maxilla when the upper and lower portions are engaged by use of an adjustable stop 414. Optionally, the adjustable stop 414 is optionally configured to connect the upper and lower portions in the clinically beneficial position.

The connectors may take various forms, some of which are currently utilized in oral appliance construction to maintain the predetermined clinically beneficial orientation.

Examples include wings, hooks, pockets, bars, trays, rails, hinges, arms, elastics, elastic bands, rigid connectors, post connectors, and/or splints. Optionally, at least a portion of the connector is removably fixed to the upper or lower portions. Optionally, at least a portion of the connector is non-removably fixed to the upper or lower portions.

Optionally, the connector comprises a mandibular portion integral to the lower portion and a maxillary portion integral to the upper portion. When the upper and lower portions are engaged, the mandibular and maxillary connector portions optionally connect the upper and lower portions to position the mandible of the subject in the predetermined clinical beneficial orientation relative to the maxilla. The mandibular and maxillary connector portions may be positioned on the sides of the upper and lower portions. Optionally, the mandibular and maxillary connector portions are positioned on the front of the upper and lower portions.

The prospectively determined clinically beneficial orientation is optionally able to be maintained by one or more different types of connector and/or tray geometries. Prior to manufacture, a professional such as a dentist may be able to select their preferred trays or connector geometry that will be used to maintain the clinically beneficial orientation. Optionally, the various types of connectors that may be used to achieve the clinically beneficial orientation may be made by use of a computer program. Optionally, the selection of which connector and/or tray geometry that is to be used to maintain the clinically beneficial position may be made by use of a computer program that will then be used to create the data set needed for manufacture of the appliance.

The methods described above for producing a device for treatment of a sleep disorder or condition include positioning the mandible of the subject in a clinically beneficial orientation relative to the maxilla of the subject. The position of the mandible relative to the maxilla is optionally registered. The registered position is then used to manufacture a device that positions the mandible in the clinically beneficial orientation relative to the maxilla.

The registered position is optionally used to manufacture at least a second device that positions the mandible in the clinically beneficial orientation or into a second or additional clinically beneficial orientation. For example, the mandible of the subject may be positioned into a second clinically beneficial orientation relative the maxilla of the subject and the second position of the mandible relative to the maxilla can be registered. The registered second position is then used to manufacture a device that positions the mandible in the second clinically beneficial orientation relative to the maxilla.

Figure 9:
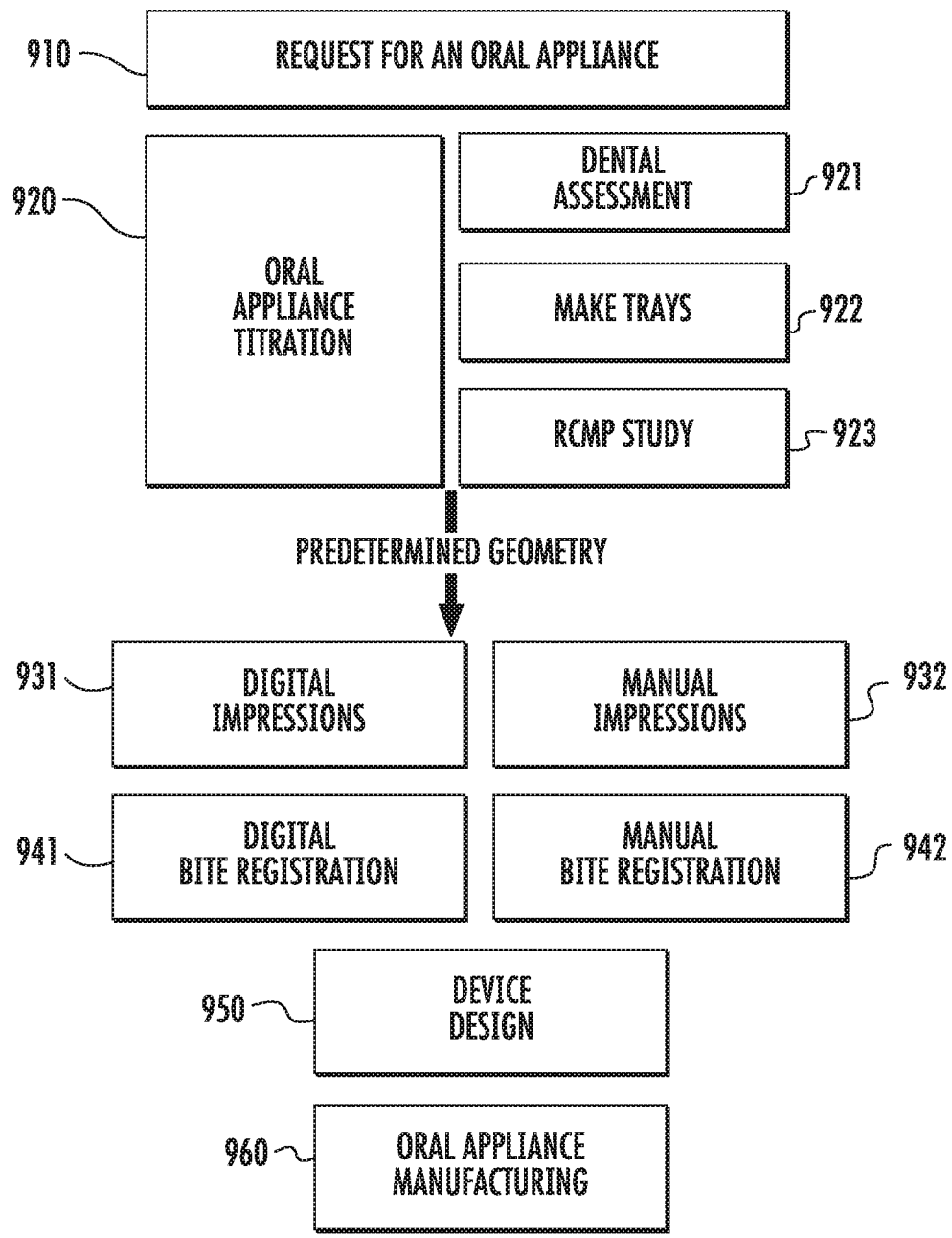
FIG. 9 is a flow chart showing an example of obtaining the predetermined geometry from an RCMP titration to manufacture an oral appliance.

FIG. 9 is a flow chart showing an example method of obtaining a predetermined geometry from an RCMP titration study 920 and using it to manufacture an oral appliance 960. Optionally, an oral appliance is requested by a patient, physician or dental professional 910 and is sent for a titration study 920 to determine if they are a suitable candidate and to determine the predetermined geometry. First, the dentition is assessed by a professional 921 and the titration trays (502,504) are created 922. The patient is then sent for an RCMP study 923. The predetermined geometry is sent to the professional for manufacturing the device. The professional records the dental anatomy via a digital (931) or manual (932) impression technique. The professional records the bite registration of the relative position of the mandible to the maxilla in the predetermined geometry also with a digital scan (941) or also with a traditional bite registration technique (942). Optionally, the impressions are taken by a manual technique (932) and the impressions are scanned and combined with the digital registration of the bite (941). The information is entered into software, that allows the professional to visualize and design the device (950) by further adjusting the predetermined geometry either for therapeutic or comfort effect. The device design (950) may also allow for selection of the desired type of connector. The data file is then sent to manufacture the device (960).

Also provided are methods for treatment of a sleep disorder or condition in a subject. Example methods include positioning an oral appliance in the mouth of the subject, wherein the oral appliance maintains the mandible of the subject in a predetermined clinically beneficial orientation relative to the maxilla of the subject.

As described throughout, an oral appliance may have an upper portion configured to receive at least one maxillary tooth of the subject and a lower portion configured to receive at least one mandibular tooth of the subject. The upper and lower portions are engageable such that the portions maintain a restricted orientation relative to each other when engaged. The engaged restricted orientation maintains the mandible of the subject in a predetermined clinically beneficial orientation relative to the maxilla of the subject.

The predetermined clinically relevant position is optionally determined by titration of the mandible relative to the maxilla while the subject is asleep. The mandible of the subject may also optionally be maintained in a second clinically beneficial orientation relative to the maxilla of the subject.

Furthermore, the mandible of the subject may optionally be maintained in a series of clinically beneficial orientations relative to the maxilla of the subject. In these examples, the second clinically beneficial orientation is optionally maintained by a second oral appliance. The series of successive clinically relevant beneficial orientations may be maintained by a series of successive oral appliances. The second or each successive oral appliance includes an upper portion configured to receive at least one maxillary tooth of the subject and a lower portion configured to receive at least one mandibular tooth of the subject.

Also provided are kits for treatment of a sleep disorder or condition in a subject. An example kit includes a first oral appliance comprising an upper portion configured to receive at least one maxillary tooth of the subject and a lower portion configured to receive at least one mandibular tooth of the subject. The upper and lower portions are engageable such that the portions maintain a restricted orientation relative to each other when engaged. The engaged restricted orientation is configured to maintain a minimal level of repositioning of mandible relative to the maxilla in at least one degree of freedom.

The kit further comprises a second oral appliance having an upper portion configured to receive at least one maxillary tooth of the subject and a lower portion configured to receive at least one mandibular tooth of the subject. The upper and lower portions are engageable such that the portions maintain a restricted orientation relative to each other when engaged. The engaged restricted orientation is configured to maintain a minimal level of repositioning of mandible relative to the maxilla in at least one degree of freedom. Optionally, the restricted orientation of the first and second oral appliances maintain a minimal level of repositioning of the mandible relative to the maxilla in two, three, four, five or six degrees of freedom.

Optionally, the kit further comprises at least one additional oral appliance. Each additional appliance comprises an upper portion configured to receive at least one maxillary tooth of the subject and a lower portion configured to receive at least one mandibular tooth. The upper and lower portions are engageable such that the portions maintain a restricted orientation relative to each other when engaged. The engaged restricted orientation is configured to maintain a minimal level of repositioning of mandible relative to the maxilla in at least one degree of freedom.

Optionally, the kit further comprises at least one oral appliance that is used to titrate the mandible of a subject into a clinically beneficial orientation relative to the maxilla of the subject. The appliance comprises an upper tray having a geometry configured to communicate with a plurality of the subject's maxillary teeth, wherein the geometry is at least partially determined from a digital scan of the maxillary teeth; and a lower tray having a geometry configured to communicate with a plurality of the subject's mandibular teeth, wherein the geometry is at least partially determined from a digital scan of the mandibular teeth. The device is operatively engageable with titration appliance and the upper and lower portions are not engageable such that the portions do not maintain a restricted orientation relative to each other when engaged. Instead, the upper and the lower trays are able to move relative to each other such that in combination with a titration appliance, multiple positions can be held and tested.

One or more of the oral appliances, as described throughout, are optionally configured to position the mandible of the subject relative to the maxilla of the subject in a predetermined clinically beneficial orientation. Each oral appliance of a series is optionally configured to progressively position the mandible of the subject relative to the maxilla of the subject towards a predetermined clinically beneficial orientation. The upper and lower portions have geometries configured to communicate with a plurality of the maxillary and mandibular teeth respectfully. The geometries are optionally at least partially determined from a digital scan of the maxillary and mandibular teeth respectfully.

During the course of the therapy, a new appliance may be ordered to further adjust the position of the mandible. The replacement device may be as part of a prescribed therapeutic plan created at the start of therapy (gradual adjustment to a new position) or it may be as a result of new information gathered during the therapy. This may occur as a result of a follow on sleep test that shows a revised therapeutic position due to changes to the bite that result from usage of the device, changes in weight, age or other factors. A replacement geometry may also be provided due to changes in temporal mandibular joint issues, tooth movement or other dental issues.

Example 1

The efficacy of using the output from a technician controlled RCMP titration device 500 to determine the geometry of an oral appliance was determined. Testing was performed by a dental investigator and/or one or more sleep physicians as described below on 65 different subjects with symptoms of obstructive sleep apnea.

Each subject received a two night baseline, pre-treatment, respiratory evaluation in the home using a portable sleep monitor. Each subject was then evaluated by the dental co-investigator and fitted with upper and lower dental titration trays (502 and 504) filled with the impression material. The dentist measured the maximum retrusion and protrusion values from the scale on the titration trays. On the night of the titration study the values provided by the dentist, for maximum retrusion and protrusion, were entered into the RCMP titration software. The titration trays were attached to the mandibular positioner and the position of the trays was adjusted by the manually adjustable knob to near full retrusion. The trays were then inserted into the subject's mouth and used for the duration of the titration study. Once the patient was asleep, the technician protruded the mandible step wise at a minimum 0.2 mm per step, using the RCMP titration device 500, until all evidence of pharyngeal obstruction (apnea or hypopnea) was eliminated in non-REM and REM sleep or until maximum protrusion was reached.

The study was scored by a polysomnographic technologist to identify respiratory disturbances. The results of the RCMP titration were reviewed without knowing patient specific information or other clinical data related to the subject to make a prospective prediction regarding therapeutic outcome. A strict set of prospectively determined criteria for the prediction were followed. Subjects were labeled a favorable candidate (predicted success) if a minimum of 5 min of REM supine was achieved with less than 1 event for every 5 minutes within the REM period; or, if no REM supine was achieved, a minimum of 5 min of REM lateral was achieved with less than 1 event per 5 minutes and the subject demonstrated in the baseline study that they spent the majority of the night in the lateral position (>50%). Subjects were labeled as unfavorable candidates (predicted failures) if more than 1 event was observed for every 5 minutes within the REM period at near maximum protrusion (within 1 mm). Otherwise, the subjects were labeled as inconclusive due to inadequate data.

For subjects labeled favorable candidates (predicted success), the protrusive position at which the obstruction was removed (as recorded on the scored PSG data) was recorded by the technician and forwarded to the dental co-investigator. For subjects labeled unfavorable candidates (predicted failure) and inconclusive, a 70 percent of full protrusion was recorded as the sham position for use by the dental co-investigator. The positions, actual and sham, were used to manufacture the subjects' permanent mandibular repositioning appliance (MRA); a Somnomed MAS Acrylic oral appliance. The subject and the dental co-investigator were blinded to the results of the RCMP polysomnographic study (i.e., to the prediction of favorable or unfavorable candidate) made by the clinical co-investigator. An outcome, post-treatment, respiratory evaluation during sleep using the same portable monitor used for baseline studies was performed on two nights in the home with the mandibular repositioning appliance (MRA) in place at the target protrusive distance.

Successful treatment with MRA was defined prospectively as achieving a respiratory disturbance index (RDI) with the appliance set at target protrusion (number of apneas and hypopneas per hour) by the automated analysis on the post treatment portable monitoring test less than 10/hr.

Thirty-three subjects were predicted to be failures with oral appliance therapy and twenty-six were predicted to be therapeutic successes, and six inconclusive. For patients who were predicted successes, mean target protrusion was 80.7% of maximum. At the target protrusion, 25 of the 26 patients were effectively treated (positive predictive value 96.1%). The remaining patient was effectively treated, however not at the target setting.

The results demonstrate that the RCMP test can effectively identify the clinically beneficial orientation and use this information to set the geometry of an oral appliance.

Example 2

A study to test the efficacy of using the output from an automated RCMP titration study to determine the geometry of an oral appliance was performed. The study was performed by comparing the geometry predicted for a patient by the manual titration study with the geometry predicted by the automated RCMP.

Seven patients that had been predicted successful by the previous study were recruited and subjected to an overnight titration test at a sleep centre with the automated RCMP device. As part of the previous study with the manual RCMP, each subject received a two night baseline, pre-treatment, respiratory evaluation in the home using a portable sleep monitor. Each subject was then evaluated by the dental co-investigator and fitted with upper and lower dental titration trays filled with the impression material. The dentist measured the maximum retrusion and protrusion values from the scale on the titration trays. The patients were studied with the manual RCMP and were determined to be successful candidates for oral appliance therapy. A target protrusive setting was determined according to the methods described in Example 1, and the position was used to manufacture the subjects' permanent mandibular repositioning appliance (MRA); a Somnomed MAS Acrylic oral appliance. An outcome, post-treatment, respiratory evaluation during sleep using the same portable monitor used for baseline studies was performed on two nights in the home with the mandibular repositioning appliance (MRA) in place to confirm the successful performance of the MRA at the target protrusion setting.

On the night of the automated RCMP study, a trained polysomnography technician entered the same values of retrusion and protrusion into the RCMP titration software. The titration trays were attached to the mandibular positioner and the position of the trays was adjusted by the manually adjustable knob to near full retrusion. The trays were then inserted into the subject's mouth and used for the duration of the titration study. Once the patient was asleep, the RCMP device was controlled by a decision making computer algorithm. The algorithm continuously receives feedback information ($SaO_2$-oxygen saturation and naris specific air flow) and makes moment-to-moment decisions regarding mandibular positioning. The collected data was analysed by methods similar to the manual RCMP to determine if the subject is a suitable candidate for oral appliance therapy and to provide the target protrusive distance. In all seven subjects, the analysis predicted a target protrusive distance that had been previously determined to be clinically beneficial in the previous manual RCMP study.

Example 3

One subject from the RCMP trial described in Example 1 was provided with an oral appliance manufactured to the target protrusive position, or clinically beneficial position, as determined from the RCMP test. First, a laser scan of the subject's dentition was obtained using parallel confocal imaging, which utilizes laser and optical scanning to digitally capture the surfaces and contours of the subject's teeth (Align Technology, Inc., San Jose, Calif.) and a digital model of the subject's teeth was provided. The model was manipulated using third party software (AutoCAD®, Autodesk, Inc., San Rafael, Calif.) to include right and left mandibular and maxilla connector portions, similar to the appliance described in FIG. 1 in which the connector portions were designed to seat against the opposing surfaces, such that the predetermined clinically relevant beneficial orientation was maintained. Using an SLA process, a SomnoDent® (Somnomed Ltd., Australia) custom fit appliance, adjusted to the clinically beneficial position, was provided to the subject. The SomnoDent® custom fit appliance was adjusted to the target protrusion of 17 mm. Using an articulator, a dental professional verified that a precise bite registration and transfer occurred, and that the manufactured appliance did hold the subject at the clinically beneficial position as described. The subject wore the appliance overnight with a home monitor to verify that the protrusive position provided the desired therapy. The subject was found to be successfully treated (RDI<10 events per hour, and a 50% reduction from baseline).

A number of embodiments of the invention have been described. Nevertheless, it will be understood that various modifications may be made without departing from the spirit and scope of the invention. Accordingly, other embodiments are within the scope of the following claims.

Disclosed are materials, systems, devices, compositions, and components that can be used for, can be used in conjunction with, can be used in preparation for, or are products of the disclosed methods, systems and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a method is disclosed and discussed each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the materials for which they are cited are hereby specifically incorporated by reference in their entireties.

What is claimed is:

1. A method for producing a device for treatment of a sleep disorder or condition, comprising:
positioning the mandible of a subject in a clinically beneficial orientation relative to the maxilla of the subject;
registering a position of the mandible in the clinically beneficial orientation relative to the maxilla; and
using the registered position to manufacture a device that positions the mandible in the clinically beneficial orientation relative to the maxilla, wherein the clinically beneficial orientation of the mandible relative to the maxilla is determined by a titration of the mandible relative to the maxilla while the subject is asleep.

2. The method of claim 1, wherein the position of the mandible relative to the maxilla is determined using a two dimensional coordinate system.

3. The method of claim 2, wherein the two dimensional coordinate system comprises an axis residing in the occlusal plane of the maxillary teeth and a second axis perpendicular to the occlusal plane of the maxillary teeth.

4. The method of claim 2, wherein the two dimensional coordinate system comprises a first axis residing in the occlusal plane of the maxillary teeth and extends from the inter-incisal space of the upper incisors and substantially along the midline of the maxillary teeth.

5. The method of claim 4, wherein the two dimensional coordinate system comprises a second axis residing perpendicular to the occlusal plane of the maxillary teeth and intersecting the first axis at the inter-incisal space of the upper incisors.

6. The method of claim 1, wherein the position of the mandible relative to the maxilla is determined using a three dimensional coordinate system.

7. The method of claim 6, wherein the three dimensional coordinate system comprises an axis residing in the occlusal plane of the maxillary teeth and a second axis perpendicular to the occlusal plane of the maxillary teeth.

8. The method of claim 6, wherein the three dimensional coordinate system comprises a first axis residing in the occlusal plane of the maxillary teeth and extends from the inter-incisal space of the upper incisors and substantially along the midline of the maxillary teeth.

9. The method of claim 8, wherein the three dimensional coordinate system comprises a second axis residing perpendicular to the occlusal plane of the maxillary teeth and intersecting the first axis at the inter-incisal space of the upper incisors.

10. The method of claim 9, wherein the three dimensional coordinate system comprises a third axis residing in the occlusal plane of the maxillary teeth, wherein the third axis is perpendicular to the second axis and intersects the first and second axes at the inter- incisal space of the upper incisors.

11. The method of claim 1, wherein the sleep disorder or condition is selected from the group consisting of sleep apnea, obstructive sleep apnea, central sleep apnea, high upper airway resistance and snoring.

12. The method of claim 1, further comprising using the registered position to manufacture at least a second device that positions the mandible in the clinically beneficial orientation or into a second or additional clinically beneficial orientation.

13. The method of claim 1, further comprising:
positioning the mandible of the subject into a second clinically beneficial orientation relative the maxilla of the subject;
registering a second position of the mandible in the second clinically beneficial orientation relative to the maxilla; and
using the registered second position to manufacture a device that positions the mandible in the second clinically beneficial orientation relative to the maxilla.

14. The method of claim 1, further comprising obtaining a digital scan of one or more maxillary teeth of the subject, wherein the digital scan of the one or more maxillary teeth is used with the registered position to manufacture the device.

15. The method of claim 1, further comprising obtaining a digital scan of one or more mandibular teeth of the subject, wherein the digital scan of the one or more mandibular teeth is used with the registered position to manufacture the device.

16. The method of claim 1, further comprising obtaining a digital scan of one or more maxillary teeth of the subject, wherein the digital scan of the one or more maxillary teeth is used to manufacture at least a second device that positions the mandible in the clinically beneficial orientation or into a second or additional clinically beneficial orientation.

17. The method of claim 1, further comprising obtaining a digital scan of one or more mandibular teeth of the subject, wherein the digital scan of the one or more mandibular teeth is used to manufacture at least a second device that positions the mandible in the clinically beneficial orientation or into a second or additional clinically beneficial orientation.

18. The method of claim 1, wherein the mandible is positioned in the clinically beneficial orientation with the use of a titration device.

19. The method of claim 1, wherein the mandible is positioned in the clinically beneficial orientation with the use of a jig device.

20. The method of claim 1, further comprising receiving the clinically beneficial orientation of the mandible of the subject relative to the maxilla of the subject.

* * * * *